US008802840B2

(12) United States Patent
Francom et al.

(10) Patent No.: US 8,802,840 B2
(45) Date of Patent: Aug. 12, 2014

(54) BICYCLIC NUCLEOSIDES AND NUCLEOTIDES AS THERAPEUTIC AGENTS

(75) Inventors: Paula Francom, Notting Hill (AU); Roland Henry Nearn, Chelsea Heights (AU); Alistair George Draffan, St Kilda East (AU); John Nicholas Lambert, Blackburn South (AU); Silas Bond, Lynbrook (AU)

(73) Assignee: Biota Scientific Management Pty Ltd., Notting Hill, Victoria (AU)

( * ) Notice: Subject to any disclaimer, the term of this patent is extended or adjusted under 35 U.S.C. 154(b) by 1443 days.

(21) Appl. No.: 11/908,019

(22) PCT Filed: Mar. 8, 2006

(86) PCT No.: PCT/AU2006/000303
§ 371 (c)(1),
(2), (4) Date: Apr. 9, 2008

(87) PCT Pub. No.: WO2006/094347
PCT Pub. Date: Sep. 14, 2006

(65) Prior Publication Data
US 2009/0004138 A1    Jan. 1, 2009
US 2010/0291031 A2   Nov. 18, 2010

Related U.S. Application Data

(60) Provisional application No. 60/661,665, filed on Mar. 8, 2005.

(51) Int. Cl.
*A61K 31/7068* (2006.01)
*C07H 19/23* (2006.01)
*A61K 38/21* (2006.01)

(52) U.S. Cl.
USPC ........... 536/27.13; 514/23; 514/43; 536/18.7; 536/29.2; 536/22.1; 424/85.4

(58) Field of Classification Search
USPC ........... 536/18.7, 29.2, 27.13, 22.1; 424/85.4; 514/23, 43
See application file for complete search history.

(56) References Cited

U.S. PATENT DOCUMENTS

| 4,965,350 A | 10/1990 | Inoue et al. |
| 6,063,628 A | 5/2000 | Loeb et al. |
| 2003/0130226 A1 | 7/2003 | Loakes et al. |
| 2005/0043268 A1 | 2/2005 | Loakes et al. |

FOREIGN PATENT DOCUMENTS

| EP | 0 235 301 B1 | 7/1992 |
| JP | 01143895 A | 6/1989 |
| WO | WO 98/18324 A1 | 5/1998 |
| WO | WO 99/06422 A2 | 2/1999 |
| WO | WO 99/43691 A1 | 9/1999 |
| WO | WO 01/16312 A3 | 3/2001 |
| WO | WO 01/32153 A2 | 5/2001 |
| WO | WO 01/60315 A2 | 8/2001 |
| WO | WO 01/79246 A2 | 10/2001 |
| WO | WO 01/90121 A2 | 11/2001 |
| WO | WO 01/92282 A2 | 12/2001 |
| WO | WO 02/18404 A2 | 3/2002 |
| WO | WO 02/057287 A2 | 7/2002 |
| WO | WO 02/057425 A2 | 7/2002 |
| WO | WO 02/062816 A1 | 8/2002 |
| WO | WO 03/039450 A2 | 5/2003 |
| WO | WO 03/072757 A2 | 9/2003 |
| WO | WO 03/073989 A2 | 9/2003 |
| WO | WO 2004/058792 A1 | 7/2004 |

OTHER PUBLICATIONS

Bartenschlager and Lohmann, "Replication of hepatitis C virus," J Gen Virology 81:1631-1648, 2000.
Bergstrom and Ruth, "Preparation of C-5 Mercurated Pyrimidine Nucleosides," J Carbohydrates-Nucleosides-Nucleotides 4(5):257-269, 1977.
Bergstrom et al., "Pyrido[2,3-d]pyrimidine Nucleosides. Synthesis via Cyclization of C-5-Substituted Cytidines," J Org Chem 47:2174-2178, 1982.
Blight et al., "Efficient Initiation of HCV RNA Replication in Cell Culture," Science 290:1972-1974, Dec. 8, 2000.
Chan et al., "2-Amino-6-arylsulfonylbenzonitriles as Non-nucleoside Reverse Transcriptase Inhibitors of HIV-1," J Med Chem 44:1866-1882, 2001.
Delaney et al., "Resistance of hepatitis B virus to antiviral drugs: current aspects and directions for future investigation," Antiviral Chemistry & Chemotherapy 12:1-35, 2001.
Dhanak et al., "Identification and Biological Characterization of Heterocyclic Inhibitors of the Hepatitis C Virus RNA-dependent RNA Polymerase," J Biological Chem 277(41):38322-38327, Oct. 11, 2002.
Durland et al., "Selective Binding of Pyrido[2,3-d]pyrimidine 2'-Deoxyribonucleoside to AT Base Pairs in Antiparallel Triple Helices," Bioconjugate Chem 6:278-282, 1995.
Dymock et al., "Novel approaches to the treatment of hepatitis C virus infection," Antiviral Chemistry & Chemotherapy 11:79-96, 2000.
Eldrup et al., "Structure-Activity Relationship of Heterobase-Modified 2'-C-Methyl Ribonucleosides as Inhibitors of Hepatitis C Virus RNA Replication," J Med Chem 47:5284-5297, 2004.
Inoue et al., "Synthesis and hybridization of dodecadeoxyribonucleotides containing a fluorescent pyridopyrimidine deoxynucleoside," Nucleic Acids Research 13(19):7119-7128, 1985.
Itoh et al., "Improved Procedures for the Syntheses of Pyrido- and Pyrrolo[2,3-d]Pyrimidines, and Ribosides Thereof," Chem Pharm Bull 37(12):3184-3190, 1989.
Kimpton et al., "Detection of Replication-Competent and Pseudotyped Human Immunodeficiency Virus with a Sensitive Cell Line on the Basis of Activation of an Integrated β-Galactosidase Gene," J Virology 66(4):2232-2239, Apr. 1992.

(Continued)

*Primary Examiner* — Savitha Rao
(74) *Attorney, Agent, or Firm* — B. Aaron Schulman, Esq.; Stites & Harbison, PLLC

(57) ABSTRACT

The invention relates to the use of bicyclic nucleosides and nucleotides based on formula (II) for the treatment of infectious diseases, and in particular, viral infections.

20 Claims, No Drawings

(56) References Cited

OTHER PUBLICATIONS

Korba and Gerin, "Use of a standardized cell culture assay to assess activities of nucleoside analogs against hepatitis B virus replication," Antiviral Research 19:55-70, 1992.

Lohmann et al., "Replication of Subgenomic Hepatitis C Virus RNAs in a Hepatoma Cell Line," Science 285:110-113, Jul. 2, 1999.

Lohmann et al., "Mutations in Hepatitis C Virus RNAs Conferring Cell Culture Adaptation," J Virology 75 (3):1437-1449, Feb. 2001.

Makishima et al., "Induction of differentiation of human myeloid leukemia HL-60 cells by novel pyrimidine nucleoside analogs," Biochimica et Biophysica Acta 1094:1-7, 1991.

Matulic-Adamic et al., "Functionalized Nucleoside 5'-triphosphates for In Vitro Selection of New Catalytic Ribonucleic Acids," Bioorganic & Medicinal Chemistry Letters 10:1299-1302, 2000.

Pai et al., "Inhibition of Hepatitis B Virus by a Novel L-Nucleoside, 2'-Fluoro-5-Methyl-β-L-Arabinofuranosyl Uracil," Antimicrobial Agents and Chemotherapy 40(2):380-386, Feb. 1996.

Pietschmann et al., "Persistent and Transient Replication of Full-Length Hepatitis C Virus Genomes in Cell Culture," J Virology 76(8):4008-4021, Apr. 2002.

Randall and Rice, "Hepatitis C virus cell culture replication systems: their potential use for the development of antiviral therapies," Current Opinion in Infectious Diseases 14:743-747, 2001.

Ranjith-Kumar et al., "Terminal Nucleotidyl Transferase Activity of Recombinant Flaviviridae RNA-Dependent RNA Polymerases: Implication for Viral RNA Synthesis," J Virology 75(18):8615-8623, Sep. 2001.

Sako, "Product Class 19: pyridopyrimidines," in Science of Synthesis: Houben-Weyl Methods of Molecular Transformations, Category 2, vol. 16, Georg Thieme Verlag, Stuttgart, 2003, pp. 1155-1267.

Schinazi et al., "Activities of 3'-Azido-3'-Deoxythymidine Nucleotide Dimers in Primary Lymphocytes Infected with Human Immunodeficiency Virus Type 1," Antimicrobial Agents and Chemotherapy 34(6):1061-1067, Jun. 1990.

Schinazi et al., "Selective Inhibition of Human Immunodeficiency Viruses by Racemates and Enantiomers of cis-5-Fluoro-1-[2-(Hydroxymethyl)-1,3-Oxathiolan-5-yl]Cytosine," Antimicrobial Agents and Chemotherapy 36 (11):2423-2431, Nov. 1992.

Schinazi et al., "Characterization of Human Immunodeficiency Viruses Resistant to Oxathiolane-Cytosine Nucleosides," Antimicrobial Agents and Chemotherapy 37(4):875-881, Apr. 1993.

Shen et al., "(E)-5-[2-(Methoxycarbonyl)ethenyl]-cytidine as a Chemical Actinometer for Germicidal UV Radiation," Environ Sci Technol 39(10):3826-3832, 2005.

Staubli and Dervan, "Sequence specificity of the non-natural pyrido[2,3-d]pyrimidine nucleoside in triple helix formation," Nucleic Acids Research 22(13):2637-2642, 1994.

Wagner et al., "Pronucleotides: Toward the In Vivo Delivery of Antiviral and Anticancer Nucleotides," Med Res Rev 20:417-451, 2000.

Whale et al., "The Synthesis of 5-substituted-2,4-Dimethoxypyrimidines and Some Related Nucleoside Analogues," Nucleosides & Nucleotides 11(7):1425-1442, 1992.

Berry & Associates Catalogue No. PYA11100; 3-(2'-Deoxy-β-D-2-ribofuranosyl)pyrido[2,3-d]pyrimidine-2,7(8H)-dione [downloaded from www.berryassoc.com, Feb. 4, 2008].

BICYCLIC NUCLEOSIDES AND NUCLEOTIDES AS THERAPEUTIC AGENTS

FIELD OF THE INVENTION

The present invention relates to the use of bicyclic nucleosides and nucleotides for the treatment of infectious diseases, including viral infections, novel bicyclic nucleosides and nucleotides and methods for their manufacture.

BACKGROUND OF THE INVENTION

Viral infections are a major threat to human health and account for many serious infectious diseases. The most notable viruses are the blood-borne viruses (BBV), which include hepatitis C virus (HCV), hepatitis B virus (HBV) and human immunodeficiency virus (HIV) which are all linked by their mode of transmission, ie. through blood or bodily fluids.

The Flaviviridae is a group of positive single-stranded RNA viruses with a genome size from 9-15 kb. The Flaviviridae consists of various genera including:
1. Flaviviruses: This genus includes the Dengue virus, Japanese Tick-Borne and the Yellow Fever virus. Apart from these major groups, there are some additional Flaviviruses that are unclassified.
2. Hepaciviruses: This genus contains only one species, the Hepatitis C virus (HCV), which is composed of many genotypes and subtypes.

HCV is a major cause of viral hepatitis and has infected more than 200 million people worldwide. Current treatment for HCV infection is restricted to immunotherapy with interferon-α alone or in combination with ribavirin, a nucleoside analog. This treatment is effective in only about half the patient population. Therefore, there is an urgent need for new HCV drugs. Hepatitis C virus comprises a positive-strand RNA genome enclosed in a nucleocapsid and lipid envelope and consists of approximately 9600 ribonucleotides, which encodes a polyprotein of about 3000 amino acids (Dymock et al. *Antiviral Chemistry & Chemotherapy* 2000, 11, 79). A HCV protein, NS5B, released from the polyprotein, possesses polymerase activity and is involved in the synthesis of double-stranded RNA from the single-stranded viral RNA genome that serves as the template. The reproduction of HCV virus may be prevented through the manipulation of NS5B's polymerase activity. The inhibition of NS5B protein would suppress or prevent the formation of the double-stranded HCV RNA. Alternatively, a nucleoside analog also may be incorporated into the extending RNA strand and act as a chain-terminator. Furthermore, a deteriorating nucleoside analog also may be incorporated into the extending RNA, which may cause mutagenic damage to the viral genome. Recently, several PCT patent applications (WO 99/43691, WO 01/32153, WO 01/60315, WO 01/79246, WO 01/90121, WO 01/92282, WO 02/18404, WO 02/057287, WO 02/057425) have described nucleoside analogs as anti-HCV agents in in vitro assays.

HBV has acutely infected almost a third of the world's human population, and about 5% of the infected are chronic carriers of the virus (Delaney I V et al., *Antiviral Chemistry & Chemotherapy* 2001, 12, 1-35). Chronic HBV infection causes liver damage that frequently progresses to cirrhosis and/or liver cancer later in the life. Despite the availability and widespread use of effective vaccines and chemotherapy, the number of chronic carriers approaches 400 million worldwide. Therefore, more effective anti-HBV drugs need to be developed.

HIV causes progressive degeneration of the immune system, leading to the development of AIDS. A number of drugs have been used clinically, including reverse transcriptase inhibitors and protease inhibitors. Currently, combination therapies are used widely for the treatment of AIDS in order to reduce the drug resistance. Despite the progress in the development of anti-HIV drugs, AIDS is still one of the leading epidemic diseases.

Apart from the BBV's discussed above certain other acute viral infections also impose a great threat to human life, including the HSV, CMV, influenza viruses, West Nile virus, SARS virus, small pox, EBV, VZV and RSV. Accordingly, this highlights the continued need for the development of different antiviral drugs.

Bacterial infections have long been the sources of many infectious diseases. The widespread use of antibiotics has produced many new strains of life-threatening antibiotic resistant bacteria. Fungal infections are another type of infectious diseases, some of which also can be life-threatening. There is an ever increasing demand for the treatment of bacterial and fungal infections. As such, antimicrobial drugs based on new mechanisms of action are especially important.

Nucleoside drugs have been used clinically for decades for the treatment of viral infections and proliferative disorders such as cancer. Most of the nucleoside drugs are classified as antimetabolites. After they enter cells, nucleoside analogs are phosphorylated successively to nucleoside 5'-monophosphates, 5'-diphosphates, and 5'-triphosphates. In most cases, nucleoside triphosphates, e.g., 3'-azido-3'-deoxythymidine triphosphate (AZT, an anti-HIV drug) and arabinosylcytosine triphosphate (cytarabine, an anticancer drug), are the active chemical entities that inhibit DNA or RNA synthesis, through a competitive inhibition of polymerases and subsequent incorporation of modified nucleotides into DNA or RNA sequences. In a few cases, nucleoside analogs exert effects at lower phosphate levels. For instance, 5-fluoro-2'-deoxyuridine 5'-monophosphate (an anticancer drug) and 2',2'-difluoro-2'-deoxycytidine 5'-diphosphate (an anticancer drug) have been shown to inhibit thymidylate synthase and ribonucleotide reductase, respectively. Although nucleoside analogs themselves may act at the nonphosphate level such as the inhibitors of adenosine kinases and the ligands of adenosine receptors, currently, clinically-useful nucleoside drugs primarily depend on cellular activation by nucleoside kinases and nucleotide kinases.

At least, two criteria are pertinent for nucleoside antiviral drugs: 1) nucleoside analogs should anabolise to nucleotides in cells; and 2) the anabolised nucleotides should target selectively viral enzymes. In order to be phosphorylated in cells and selectively target preferred enzymes, nucleoside analogs should have favourable modifications on their sugar and base moieties. To obtain such favourable nucleoside analogs, a general approach is to generate diverse nucleoside analogs by modifying the base or the sugar, or by modifying both base and sugar moieties. Numerous examples exist in the literature for the synthesis of a variety of modified nucleosides (*Chemistry of Nucleosides and Nucleotides* Vol. 1 (1988), Vol. 2 (1991), Vol. 3 (1994), edited by L. B. Townsend, Plenum Press; *Handbook of Nucleoside Synthesis* by H. Vorbrüggen and C. Ruh-Pohlenz, John Wiley & Sons, Inc., 2001; *The Organic Chemistry of Nucleic Acids* by Y. Mizuno, Elsevier, 1986).

However, there are certain classes of nucleoside compounds that were not explored intensively for their antiviral activities before the present invention. A class of such compounds is bicyclic nucleosides which are not derived from purine bases. Disclosures of bicyclic nucleosides are very limited considering that natural adenine and guanine (purines) based ribonucleotides and deoxy derivatives thereof, have bicyclic base moieties. WO 01/92282 A2, WO 01/90121 A2 and WO 04/058792 disclose derivatives of purine nucleosides. In contrast to these publications, the present invention discloses that a certain new class of bicyclic nucleosides and nucleotides display biological activity which may be particularly useful for the treatment of infectious diseases, including viral infections.

SUMMARY OF THE INVENTION

The present invention relates to a particular class of bicyclic nucleosides, nucleotides, and derivatives thereof and their use in the treatment of microbial infections, and specifically viral infections.

In particular, the present invention provides a method for the treatment of a microbial infection, comprising administering an effective amount of a compound of the formula (I) or a pharmaceutically acceptable salt thereof;

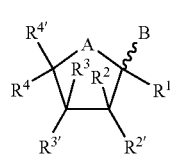
(I)

wherein:

A is O, S, $CH_2$, CHF, $CF_2$ or NR;

$R^1$, $R^2$, $R^{2'}$, $R^3$, $R^{3'}$, and $R^4$ are independently selected from the group consisting of H, halogen, OH, $N_3$, CN, optionally substituted alkyl, optionally substituted alkenyl, optionally substituted alkynyl, optionally substituted aryl, optionally substituted acyl, optionally substituted arylalkyl, optionally substituted heterocyclyl, optionally substituted heteroaryl, optionally substituted cycloalkyl, optionally substituted cycloalkenyl, optionally substituted alkyloxy, optionally substituted alkenyloxy, optionally substituted alkynoxy, optionally substituted aryloxy, optionally substituted acyloxy, optionally substituted oxyacyl, optionally substituted arylalkoxy, optionally substituted heterocycloxy, optionally substituted heteroaryloxy, optionally substituted cycloalkoxy, optionally substituted cycloalkenoxy, optionally substituted amino, optionally substituted aminoacyl, optionally substituted aminoacyloxy, optionally substituted acylamino, optionally substituted oxyacylamino, optionally substituted oxyacyloxy, optionally substituted acylimino, optionally substituted acyliminoxy, optionally substituted oxyacylimino, optionally substituted aminothioacyl, optionally substituted thioacylamino, optionally substituted aminosulfinyl, optionally substituted aminosulfonyl, optionally substituted thio, optionally substituted thioacyl, optionally substituted thioacyloxy, optionally substituted oxythioacyl, optionally substituted oxythioacyloxy, optionally substituted phosphorylamino, optionally substituted sulfinyl, optionally substituted sulfonyl, optionally substituted sulfinylamino, optionally substituted sulfonylamino, optionally substituted oxysulfinylamino, and optionally substituted oxysulfonylamino, or $R^2$ and $R^{2'}$ together or $R^3$ and $R^{3'}$ together represents =O, =S, or =L-Y' where L is N, CH, CF, CCl or CBr and Y' is H, halogen, $N_3$, methyl, ethyl or CN;

$R^{4'}$ is $—CY_2SH$, $—CY_2OH$, $—CY_2NH_2$, or $-L'-R^5$;

L' is selected from the group consisting of $—CY_2—$, $—CY_2CY_2—$, $—CY_2OCY_2—$, $—CY_2SCY_2—$ and $—CY_2NHCY_2—$;

each Y is independently selected from the group consisting of H, F, Cl, Br, OR, $C_1$-$C_6$alkyl, $C_2$-$C_6$alkenyl and $C_2$-$C_6$alkynyl, wherein $C_1$-$C_6$alkyl, $C_2$-$C_6$alkenyl, and $C_2$-$C_6$alkynyl may be optionally substituted with one or more groups selected from F, Cl, Br, OH, COOH, $COOCH_3$, SH, $SCH_3$, $NH_2$, $NHCH_3$, $N(CH_3)_2$, CN, $NO_2$, $C(O)NH_2$, $C(O)NHCH_3$, $N_3$, $C(S)NH_2$, $OCH_3$, and $OCH_2CH_3$;

$R^5$ is selected from the group consisting of OR, $NR_2$, monophosphate, diphosphate, and triphosphate, or a mono, di or triphosphate mimic;

each R is independently selected from the group consisting of H, $CF_3$, optionally substituted alkyl, optionally substituted alkenyl, optionally substituted alkynyl, optionally substituted aryl, optionally substituted acyl, optionally substituted cycloalkyl, optionally substituted cycloalkenyl, optionally substituted heteroaryl, optionally substituted heterocyclyl, and optionally substituted arylalkyl;

B is a group of formula (II)

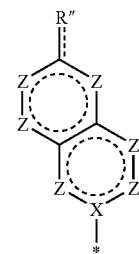
(II)

wherein, if Z is a participant in a π bond (double bond), Z is independently selected from N or C-G; or, if Z is not a participant in a π bond (double bond), Z is independently selected from O, S, Se, NR, NOR, $NNR_2$, CO, CS, CNR, SO, $S(O)_2$, SeO, $Se(O)_2$ or $C(G)_2$, wherein each G is independently selected from the group consisting of H, halogen, OR, SR, $NR_2$, NROR, $N_3$, COOR, CN, $CONR_2$, $C(S)NR_2$, C(=NR)$NR_2$, and R; and where any two adjacent Z are not both selected from O, S, and Se, or not both selected from CO, CS, CNR, SO, $S(O)_2$, SeO, and $Se(O)_2$;

wherein, if X is a participant in a π bond (double bond), X is C; or if X is not a participant in a π bond (double bond), X is CR or N;

wherein, if R" is a participant in a π bond (double bond), R" is O, S, Se, NR, NOR or $NNR_2$; or if R" is not a participant in a π bond (double bond), R" is OR, SR, F, Cl, R, or SeR; and dashed lines (- - -) indicate a possible π or double bond;

optionally in combination with one or more antiviral or antibacterial agents.

The present invention also further provides the use of a compound of formula (I) or a salt thereof;

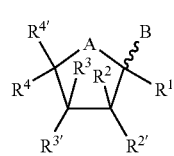
(I)

wherein:

A is O, S, CH$_2$, CHF, CF$_2$ or NR;

R$^1$, R$^2$, R$^{2'}$, R$^3$, R$^{3'}$, and R$^4$ are independently selected from the group consisting of H, halogen, OH, N$_3$, CN, optionally substituted alkyl, optionally substituted alkenyl, optionally substituted alkynyl, optionally substituted aryl, optionally substituted acyl, optionally substituted arylalkyl, optionally substituted heterocyclyl, optionally substituted heteroaryl, optionally substituted cycloalkyl, optionally substituted cycloalkenyl, optionally substituted alkyloxy, optionally substituted alkenyloxy, optionally substituted alkynoxy, optionally substituted aryloxy, optionally substituted acyloxy, optionally substituted oxyacyl, optionally substituted arylalkoxy, optionally substituted heterocycloxy, optionally substituted heteroaryloxy, optionally substituted cycloalkoxy, optionally substituted cycloalkenoxy, optionally substituted amino, optionally substituted aminoacyl, optionally substituted aminoacyloxy, optionally substituted acylamino, optionally substituted oxyacylamino, optionally substituted oxyacyloxy, optionally substituted acylimino, optionally substituted acyliminoxy, optionally substituted oxyacylimino, optionally substituted aminothioacyl, optionally substituted thioacylamino, optionally substituted aminosulfinyl, optionally substituted aminosulfonyl, optionally substituted thio, optionally substituted thioacyl, optionally substituted thioacyloxy, optionally substituted oxythioacyl, optionally substituted oxythioacyloxy, optionally substituted phosphorylamino, optionally substituted sulfinyl, optionally substituted sulfonyl, optionally substituted sulfinylamino, optionally substituted sulfonylamino, optionally substituted oxysulfinylamino, and optionally substituted oxysulfonylamino, or R$^2$ and R$^{2'}$ together or R$^3$ and R$^{3'}$ together represents =O, =S, or =L-Y' where L is N, CH, CF, CCl or CBr and Y' is H, halogen, N$_3$, methyl, ethyl or CN;

R$^{4'}$ is —CY$_2$SH, —CY$_2$OH, —CY$_2$NH$_2$, or -L'-R$^5$;

L' is selected from the group consisting of —CY$_2$—, —CY$_2$CY$_2$—, —CY$_2$OCY$_2$—, —CY$_2$SCY$_2$— and —CY$_2$NHCY$_2$—;

each Y is independently selected from the group consisting of H, F, Cl, Br, OR, C$_1$-C$_6$alkyl, C$_2$-C$_6$alkenyl and C$_2$-C$_6$alkynyl, wherein C$_1$-C$_6$alkyl, C$_2$-C$_6$alkenyl, and C$_2$-C$_6$alkynyl may be optionally substituted with one or more groups selected from F, Cl, Br, OH, COOH, COOCH$_3$, SH, SCH$_3$, NH$_2$, NHCH$_3$, N(CH$_3$)$_2$, CN, NO$_2$, C(O)NH$_2$, C(O)NHCH$_3$, N$_3$, C(S)NH$_2$, OCH$_3$, and OCH$_2$CH$_3$;

R$^5$ is selected from the group consisting of OR, NR$_2$, monophosphate, diphosphate, and triphosphate, or a mono, di or triphosphate mimic;

each R is independently selected from the group consisting of H, CF$_3$, optionally substituted alkyl, optionally substituted alkenyl, optionally substituted alkynyl, optionally substituted aryl, optionally substituted acyl, optionally substituted cycloalkyl, optionally substituted cycloalkenyl, optionally substituted heteroaryl, optionally substituted heterocyclyl, and optionally substituted arylalkyl;

B is a group of formula (II)

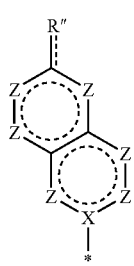

(II)

wherein, if Z is a participant in a π bond (double bond), Z is independently selected from N or C-G; or, if Z is not a participant in a π bond (double bond), Z is independently selected from O, S, Se, NR, NOR, NNR$_2$, CO, CS, CNR, SO, S(O)$_2$, SeO, Se(O)$_2$ or C(G)$_2$, wherein each G is independently selected from the group consisting of H, halogen, OR, SR, NR$_2$, NROR, N$_3$, COOR, CN, CONR$_2$, C(S)NR$_2$, C(=NR)NR$_2$, and R; and where any two adjacent Z are not both selected from O, S, and Se, or not both selected from CO, CS, CNR, SO, S(O)$_2$, SeO, and Se(O)$_2$;

wherein, if X is a participant in a π bond (double bond), X is C; or if X is not a participant in a π bond (double bond), X is CR or N;

wherein, if R" is a participant in a π bond (double bond), R" is O, S, Se, NR, NOR or NNR$_2$; or if R" is not a participant in a π bond (double bond), R" is OR, SR, F, Cl, R, or SeR; and dashed lines (- - -) indicate a possible π or double bond;

in the manufacture of a medicament for the treatment of a microbial infection.

DESCRIPTION OF THE PREFERRED EMBODIMENTS

"Alkyl" refers to monovalent alkyl groups which may be straight chained or branched and preferably have from 1 to 10 carbon atoms or more preferably 1 to 6 carbon atoms. Examples of such alkyl groups include methyl, ethyl, n-propyl, iso-propyl, n-butyl, iso-butyl, n-hexyl, and the like.

"Aryl" refers to an unsaturated aromatic carbocyclic group having a single ring (eg., phenyl) or multiple condensed rings (eg., naphthyl or anthryl), preferably having from 6 to 14 carbon atoms. Examples of aryl groups include phenyl, naphthyl and the like.

"Arylene" refers to a divalent aryl group wherein the aryl group is as described above.

"Aryloxy" refers to the group aryl-O— wherein the aryl group is as described above.

"Arylalkyl" refers to -alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Arylalkoxy" refers to the group arylalkyl-O— wherein the arylalkyl group are as described above. Such arylalkoxy groups are exemplified by benzyloxy and the like.

"Alkoxy" refers to the group alkyl-O— where the alkyl group is as described above. Examples include, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH=CH$_2$), n-propenyl (—CH$_2$CH=CH$_2$), iso-propenyl (—C(CH$_3$)=CH$_2$), but-2-enyl (—CH$_2$CH=CHCH$_3$), and the like.

"Alkenyloxy" refers to the group alkenyl-O— wherein the alkenyl group is as described above.

"Alkynyl" refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH), propargyl (—CH$_2$C≡CH), pent-2-ynyl (—CH$_2$C≡CCH$_2$—CH$_3$), and the like.

"Alkynyloxy" refers to the group alkynyl-O— wherein the alkynyl groups is as described above.

"Acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein.

"Oxyacyl" refers to groups H—OC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

"Amino" refers to the group —NR'''R''' where each R''' is independently hydrogen, alkyl, cycloalkyl, aryl, heteroaryl, and heterocyclyl and where alkyl, cycloalkyl, aryl, heteroaryl and heterocyclyl is as described herein.

"Aminoacyl" refers to the group —C(O)NR'''R''' where each R''' is independently hydrogen, alkyl, cycloalkyl, aryl, heteroaryl, and heterocyclyl and where alkyl, cycloalkyl, aryl, heteroaryl and heterocyclyl is as described herein.

"Acylamino" refers to the group —NR'''C(O)R''' where each R''' is independently hydrogen, alkyl, cycloalkyl, aryl, heteroaryl and heterocyclyl and where alkyl, cycloalkyl, aryl, heteroaryl, and heterocyclyl are as described herein.

"Acyloxy" refers to the groups —OC(O)—H, —OC(O)-alkyl, —OC(O)-aryl, —C(O)O-heteroaryl, and —C(O)O-heterocyclyl where alkyl, aryl, heteroaryl and heterocyclyl are as described herein.

"Aminoacyloxy" refers to the groups —OC(O)NR'''—H, —OC(O)NR'''-alkyl, —OC(O)NR'''-aryl, —OC(O)NR'''-heteroaryl, and —OC(O)NR'''-heterocyclyl where R''' is independently hydrogen, alkyl, cycloalkyl, aryl, heteroaryl, and heterocyclyl and where alkyl, cycloalkyl, aryl, heteroaryl and heterocyclyl is as described herein.

"Oxyacylamino" refers to the groups —NR'''C(O)OH, —NR'''C(O)O-alkyl, —NR'''C(O)O-aryl, —NR'''C(O)O-heteroaryl, and NR'''C(O)O-heterocyclyl where R''' is independently hydrogen, alkyl, cycloalkyl, aryl, heteroaryl, and heterocyclyl and where alkyl, cycloalkyl, aryl, heteroaryl and heterocyclyl is as described herein.

"Oxyacyloxy" refers to the groups —OC(O)—OH, —OC(O)O-alkyl, —O—C(O)O-aryl, —OC(O)O-heteroaryl, and —OC(O)O-heterocyclyl where alkyl, cycloalkyl, aryl, heteroaryl, and heterocyclyl are as described herein.

"Acylimino" refers to the groups —C(NR''')—R''' where each R''' is independently hydrogen, alkyl, cycloalkyl, aryl, heteroaryl and heterocyclyl and where alkyl, cycloalkyl, aryl, heteroaryl, and heterocyclyl are as described herein.

"Acyliminoxy" refers to the groups —O—C(NR''')—R''' where each R''' is independently hydrogen, alkyl, cycloalkyl, aryl, heteroaryl and heterocyclyl and where alkyl, cycloalkyl, aryl, heteroaryl, and heterocyclyl are as described herein.

"Oxyacylimino" refers to the groups —C(NR''')—OR''' where each R''' is independently hydrogen, alkyl, cycloalkyl, aryl, heteroaryl and heterocyclyl and where alkyl, cycloalkyl, aryl, heteroaryl, and heterocyclyl are as described herein.

"Cycloalkyl" refers to cyclic alkyl groups having a single cyclic ring or multiple condensed rings, preferably incorporating 3 to 8 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, and the like.

"Cycloalkenyl" refers to cyclic alkenyl groups having a single cyclic ring and at least one point of internal unsaturation, preferably incorporating 4 to 8 carbon atoms. Examples of suitable cycloalkenyl groups include, for instance, cyclobut-2-enyl, cyclopent-3-enyl, cyclohex-4-enyl, cyclooct-3-enyl and the like.

"Halo" or "halogen" refers to fluoro, chloro, bromo and iodo.

"Heteroaryl" refers to a monovalent aromatic heterocyclic group which fulfils the Hückel criteria for aromaticity (ie. contains $4n+2\pi$ electrons, is planar and conjugated) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (eg., pyridyl, pyrrolyl or N-oxides thereof or furyl) or multiple condensed rings (eg., indolizinyl, benzoimidazolyl, coumarinyl, quinolinyl, isoquinolinyl or benzothienyl).

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. The most preferred heteroatom is nitrogen.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Thio" refers to groups H—S—, alkyl-S—, cycloalkyl-S—, aryl-S—, heteroaryl-S—, and heterocyclyl-S—, where alkyl, cycloalkyl, aryl, heteroaryl and heterocyclyl are as described herein.

"Thioacyl" refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl and heterocyclyl are as described herein.

"Oxythioacyl" refers to groups HO—C(S)—, alkylO—C(S)—, cycloalkylO—C(S)—, arylO—C(S)—, heteroarylO—C(S)—, and heterocyclylO—C(S)—, where alkyl, cycloalkyl, aryl, heteroaryl and heterocyclyl are as described herein.

"Oxythioacyloxy" refers to groups HO—C(S)—O—, alkylO—C(S)—O—, cycloalkylO—C(S)—O—, arylO—C(S)—O—, heteroarylO—C(S)—O—, and heterocyclylO—C(S)—O—, where alkyl, cycloalkyl, aryl, heteroaryl and heterocyclyl are as described herein.

"Phosphorylamino" refers to the groups —NR'''—P(O)(R'''')(OR''''') where R'''' represents H, alkyl, cycloalkyl, alkenyl, or aryl, R''''' represents OR'''''' or is hydroxy or amino and R'''''' is alkyl, cycloalkyl, aryl or arylalkyl, where alkyl, amino, alkenyl, aryl, cycloalkyl, and arylalkyl are as described herein.

"Thioacyloxy" refers to groups H—C(S)—O—, alkyl-C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl" refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl and heterocyclyl are as described herein.

"Sulfonyl" refers to groups H—S(O)$_2$—, alkyl-S(O)$_2$—, cycloalkyl-S(O)$_2$—, aryl-S(O)$_2$—, heteroaryl-S(O)$_2$—, and heterocyclyl-S(O)$_2$—, where alkyl, cycloalkyl, aryl, heteroaryl and heterocyclyl are as described herein.

"Sulfinylamino" refers to groups H—S(O)—NR'''—, alkyl-S(O)—NR'''—, cycloalkyl-S(O)—NR'''—, aryl-S(O)—NR'''—, heteroaryl-S(O)—NR'''—, and heterocyclyl-S(O)—NR'''—, where R''' is independently hydrogen, alkyl, cycloalkyl, aryl, heteroaryl, and heterocyclyl and where alkyl, cycloalkyl, aryl, heteroaryl and heterocyclyl is as described herein.

"Sulfonylamino" refers to groups H—S(O)$_2$—NR'''—, alkyl-S(O)$_2$—NR'''—, cycloalkyl-S(O)$_2$—NR'''—, aryl-S(O)$_2$—NR'''—, heteroaryl-S(O)$_2$—NR'''—, and heterocyclyl-S(O)$_2$—NR'''—, where R''' is independently hydrogen, alkyl, cycloalkyl, aryl, heteroaryl, and heterocyclyl and alkyl, cycloalkyl, aryl, heteroaryl and heterocyclyl is as described herein.

"Oxysulfinylamino" refers to groups HO—S(O)—NR'''—, alkylO—S(O)—NR'''—, cycloalkylO—S(O)—NR'''—, arylO—S(O)—NR'''—, heteroarylO—S(O)—NR'''—, and heterocyclylO—S(O)—NR'''—, where R''' is independently hydrogen, alkyl, cycloalkyl, aryl, heteroaryl, and heterocyclyl and where alkyl, cycloalkyl, aryl, heteroaryl and heterocyclyl is as described herein.

"Oxysulfonylamino" refers to groups HO—S(O)$_2$—NR'''—, alkylO—S(O)$_2$—NR'''—, cycloalkylO—S(O)$_2$—NR'''—, arylO—S(O)$_2$—NR'''—, heteroarylO—S(O)$_2$—NR'''—, and heterocyclylO—S(O)$_2$—NR'''—, where R''' is independently hydrogen, alkyl, cycloalkyl, aryl, heteroaryl, and heterocyclyl and where alkyl, cycloalkyl, aryl, heteroaryl and heterocyclyl is as described herein.

"Aminothioacyl" refers to groups R'''R'''N—C(S)—, where each R''' is independently hydrogen, alkyl, cycloalkyl, aryl, heteroaryl, where heterocyclic and alkyl, cycloalkyl, aryl, heteroaryl and heterocyclyl is as described herein.

"Thioacylamino" refers to groups H—C(S)—NR'''—, alkyl-C(S)—NR'''—, cycloalkyl-C(S)—NR'''—, aryl-C(S)—NR'''—, heteroaryl-C(S)—NR'''—, and heterocyclyl-C(S)—NR'''—, where R''' is independently hydrogen, alkyl, cycloalkyl, aryl, heteroaryl, and where heterocyclyl and alkyl, cycloalkyl, aryl, heteroaryl and heterocyclyl is as described herein.

"Aminosulfinyl" refers to groups R'''R'''N—S(O)—, where each R''' is independently hydrogen, alkyl, cycloalkyl, aryl, heteroaryl, and heterocyclic and where alkyl, cycloalkyl, aryl, heteroaryl and heterocyclyl is as described herein.

"Aminosulfonyl" refers to groups R'''R'''N—S(O)$_2$—, where each R''' is independently hydrogen, alkyl, cycloalkyl, aryl, heteroaryl, and heterocyclic and where alkyl, cycloalkyl, aryl, heteroaryl and heterocyclyl is as described herein.

In this specification "optionally substituted" is taken to mean that a group may or may not be further substituted or fused (so as to form a condensed polycyclic group) with one or more groups selected from hydroxyl, acyl, alkyl, alkoxy, alkenyl, alkenyloxy, alkynyl, alkynyloxy, amino, aminoacyl, thio, arylalkyl, arylalkoxy, aryl, aryloxy, acylamino, cyano, halogen, nitro, sulfo, phosphono, phosphorylamino, phosphinyl, heteroaryl, heteroaryloxy, heterocyclyl, heterocycloxy, oxyacyl, acyloxy, oxime, oxime ether, hydrazone, oxyacylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like. For instance, an "optionally substituted amino" group may include amino acid and peptide residues.

The term "base", unless otherwise specified, refers to the base moiety of a nucleoside or nucleotide. The base moiety is the nitrogen-heterocycle portion of a nucleoside or nucleotide. The base moiety of a nucleotide of formula (I) is a bicyclic heterocycle represented by formula (II) and designated "B". The nucleoside base is attached to the sugar moiety of a nucleoside in such ways that both α and β anomers of D or L nucleosides can be produced. This is denoted by use of the ∼∼∼ bond which links the base to the sugar moiety.

The term "sugar" refers to the furanose portion of a nucleoside. The sugar moiety of formula (I) nucleosides, nucleotides and nucleotides mimics and/or prodrugs thereof may contain one or more substituents at their C1-, C2-, C3- and C4-position of the furanose. Substituents may be directed to either the α- or β-face of the furanose. The nucleoside base can be considered as a substituent at the C-1 position of the furanose and is preferably directed to the β-face of the sugar. The β-face is the side of a furanose on which a purine or pyrimidine base of natural β-D-nucleosides is present. The α-face is the side of the sugar opposite to the β-face.

Examples of a "protecting group" for O, S, or N moieties such as hydroxy or NH$_2$, includes acyl groups, silyl groups, and the like. Suitable protecting groups for these and other moieties are described by T. W., Greene and P. G. M. Wuts; *Protecting Groups in Organic Synthesis*, 3$^{rd}$ Ed, John Wiley & Sons, Inc. (1999), incorporated herein by reference.

The term "infection" or "microbial infection" refers to the infection caused by an infectious agent or microbe, such as bacteria, parasite (including protozoan), virus or fungus (including unicellular and multicellular). Examples of microbes that cause such infection include: *Acanthamoeba*, African Sleeping Sickness (Trypanosomiasis), amebiasis, American Trypanosomiasis (Chagas Disease), Bilharzia (Schistosomiasis), cryptosporidiosis (diarrheal disease, *Cryptosporidium Parvum*), Giardiasis (diarrheal disease, *Giardia lamblia*), hepatitis A, B, C, D, E, leishmaniasis (skin sores and visceral), malaria (*Plasmodium falciparum*), *Salmonella* enteritides infection (stomach cramps, diarrhea and fever), tuberculosis (*mycobacterium tuberculosis*), varicella (chicken pox), yellow fever, pneumonias, urinary tract infections (*Chlamydia* and *Mycoplasma*), meningitis and meningococcal septicemia, skin and soft tissue infections (*Staphylococcus aureus*), lower respiratory tract infections (bacterial pathogens or viral pathogens).

Common infections caused by microbes are further outlined in the following chart:

| Infection | Bacteria | Fungus | Protozoa | Virus |
|---|---|---|---|---|
| AIDS | | | | X |
| Athlete's Foot | | X | | |
| Chicken Pox | | | | X |
| Common Cold | | | | X |
| Diarrheal Disease | X | | X | X |
| Dengue | | | | X |
| Flu | | | | X |
| Genital Herpes | | | | X |
| Malaria | X | | X | |
| Meningitis | X | | | |
| Pneumonia | X | X | | |
| Sinusitis | X | X | | |
| Skin Disease | X | X | X | X |
| Strep Throat | X | | | |
| Tuberculosis | X | | | |
| Urinary Tract Infections | X | | | |
| Vaginal Infections | X | X | | |
| Viral Hepatitis | | | | X |

In relation to the therapeutic methods of the present invention the compounds of formula (I) may be particularly useful for treating a microbial infection which is a viral infection caused by an RNA virus, such as a virus belonging to group Flaviviridae, for instance Flaviviruses or HCV, or a DNA or retrovirus such as HBV or HIV. In a preferred embodiment the method of the present invention treats a viral infection caused by an RNA virus of the group Flaviviridae and in particular HCV.

The compounds of formula (I) are administered to the subject in a therapeutic effective amount. As used herein, a therapeutic effective amount is intended to include at least partially attaining the desired effect, or delaying the onset of, or inhibiting the progression of, or halting or reversing altogether the onset or progression of the particular disease of condition being treated.

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 10 g per kg of body weight per dosage. The dosage may be in the range of 1 μg to 10 g per kg of body weight per dosage, such as is in the range of 1 mg to 10 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another preferred embodiment, the dosage may be in the range of 1 mg to 100 mg per kg of body weight per dosage, such as up to 50 mg per body weight per dosage.

Suitable dosage amounts and dosing regimens can be determined by the attending physician and may depend on the particular condition being treated, the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, further antifungal and antibacterial agents, dermal penetration agents, surfactants, isotonic and absorption agents and the like. It will be understood that the compositions of the invention may also include other supplementary physiologically active agents.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Finally, formulations of these compositions in dry powder form for delivery by a dry powder inhaler offer yet another means of administration. This overcomes many of the disadvantages of the oral and intravenous routes.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

In a further embodiment, the present invention provides novel compounds, pharmaceutical compositions of said novel compounds and therapeutic applications of said novel compounds for the treatment of microbial infections.

Accordingly, in another aspect the present invention provides a compound of the formula (I) or a salt thereof;

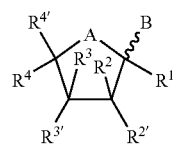

(I)

wherein:
A is O, S, $CH_2$, CHF, $CF_2$ or NR;
$R^1$, $R^2$, $R^{2'}$, $R^3$, $R^{3'}$, and $R^4$ are independently selected from the group consisting of H, halogen, OH, $N_3$, CN, optionally substituted alkyl, optionally substituted alkenyl, optionally substituted alkynyl, optionally substituted aryl, optionally substituted acyl, optionally substituted arylalkyl, optionally substituted heterocyclyl, optionally substituted heteroaryl, optionally substituted cycloalkyl, optionally substituted cycloalkenyl, optionally substituted alkyloxy, optionally substituted alkenyloxy, optionally substituted alkynoxy, optionally substituted aryloxy, optionally substituted acyloxy, optionally substituted oxyacyl, optionally substituted arylalkoxy, optionally substituted heterocycloxy, optionally substituted heteroaryloxy, optionally substituted cycloalkoxy, optionally substituted cycloalkenoxy, optionally substituted amino, optionally substituted aminoacyl, optionally substituted aminoacyloxy, optionally substituted acylamino, optionally substituted oxyacylamino, optionally substituted oxyacyloxy, optionally substituted acylimino, optionally substituted acyliminoxy, optionally substituted oxyacylimino, optionally substituted aminothioacyl, optionally substituted thioacylamino, optionally substituted aminosulfinyl, optionally substituted aminosulfonyl, optionally substituted thio, optionally substituted thioacyl, optionally substituted thioacyloxy, optionally substituted oxythioacyl, optionally substituted oxythioacyloxy, optionally substituted phosphorylamino, optionally substituted sulfinyl, optionally substituted sulfonyl, optionally substituted sulfinylamino, optionally substituted sulfonylamino, optionally substituted oxysulfinylamino, and optionally substituted oxysulfonylamino, or $R^2$ and $R^{2'}$ together or $R^3$ and $R^{3'}$ together represents =O, =S, or =L-Y' where L is N, CH, CF, CCl or CBr and Y' is H, halogen, $N_3$, methyl, ethyl or CN;

$R^{4'}$ is —$CY_2SH$, —$CY_2OH$, —$CY_2NH_2$, or -L'-$R^5$;

L' is selected from the group consisting of —$CY_2$—, —$CY_2CY_2$—, —$CY_2OCY_2$—, —$CY_2SCY_2$— and —$CY_2NHCY_2$—;

each Y is independently selected from the group consisting of H, F, Cl, Br, OR, $C_1$-$C_6$alkyl, $C_2$-$C_6$alkenyl and $C_2$-$C_6$alkynyl, wherein $C_1$-$C_6$alkyl, $C_2$-$C_6$alkenyl and $C_2$-$C_6$alkynyl may be optionally substituted with one or more groups selected from F, Cl, Br, OH, COOH, $COOCH_3$, SH, $SCH_3$, $NH_2$, $NHCH_3$, $N(CH_3)_2$, CN, $NO_2$, $C(O)NH_2$, $C(O)NHCH_3$, $N_3$, $C(S)NH_2$, $OCH_3$, and $OCH_2CH_3$;

$R^5$ is selected from the group consisting of OR, $NR_2$, monophosphate, diphosphate, and triphosphate, or a mono, di or triphosphate mimic;

each R is independently selected from the group consisting of H, $CF_3$, optionally substituted alkyl, optionally substituted alkenyl, optionally substituted alkynyl, optionally substituted aryl, optionally substituted acyl, optionally substituted cycloalkyl, optionally substituted cycloalkenyl, optionally substituted heteroaryl, optionally substituted heterocyclyl, and optionally substituted arylalkyl;

B is a group of formula (II)

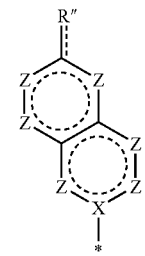

(II)

wherein, if Z is a participant in a π bond (double bond), Z is independently selected from N or C-G; or, if Z is not a participant in a π bond (double bond), Z is independently selected from O, S, Se, NR, NOR, $NNR_2$, CO, CS, CNR, SO, $S(O)_2$, SeO, $Se(O)_2$ or $C(G)_2$, wherein each G is independently selected from the group consisting of H, halogen, OR, SR, $NR_2$, NROR, $N_3$, COOR, CN, $CONR_2$, $C(S)NR_2$, $C(=NR)NR_2$, $NCONR_2$, $NCSNR_2$ and R; and where any two adjacent Z are not both selected from O, S, and Se, or not both selected from CO, CS, CNR, SO, $S(O)_2$, SeO, and $Se(O)_2$;

wherein, if X is a participant in a π bond (double bond), X is C; or if X is not a participant in a π bond (double bond), X is CR or N;

wherein, if R" is a participant in a π bond (double bond), R" is O, S, Se, NR, NOR, and $NNR_2$; or if R" is not a participant in a π bond (double bond), R" is OR, SR, F, Cl, R, or SeR;

dashed lines (- - -) indicate a possible π or double bond; and wherein when $R^{2'}$, $R^{3'}$, and $R^5$ are OH or $OC(O)CH_3$, L' is $CH_2$, A is O, and $R^1$, $R^2$, $R^3$ and $R^4$ are H, B is not the group of formula (III), formula (IV), formula (V), formula (VI), or formula (VII)

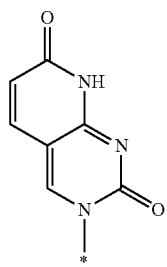 (III)

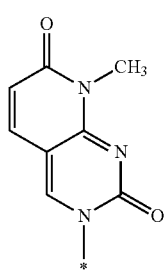 (IV)

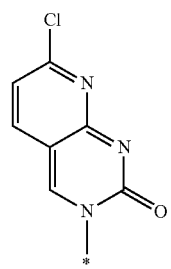 (V)

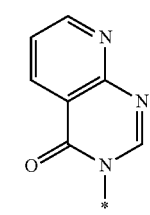 (VI)

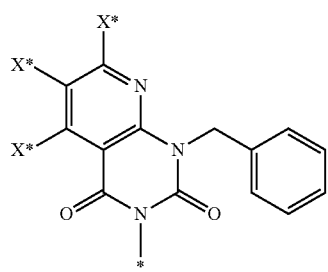 (VII)

(where all X* are H, or one of X* is $CH_3$ and the other two X* are H); when B is a group of formula (III), formula (VIII), or formula (IX)

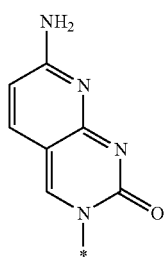 (VIII)

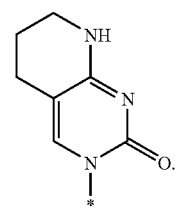 (IX)

$R^2$ and $R^{2'}$ are not both H;

when $R^2$, $R^{3'}$ and $R^5$ are OH, L' is $CH_2$, A is O and $R^1$, $R^{2'}$, $R^3$ and $R^4$ are H, B is not the group of formula (IV); and when $R^{2'}$ is F, $R^{3'}$ is OH, $R^5$ is triphosphate, L' is $CH_2$, A is O, and $R^1$, $R^2$, $R^3$ and $R^4$ are H, B is not a group of formula (X)

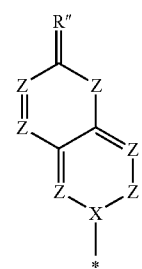 (X)

In some preferred embodiments of the invention one or more of the following definitions apply:

The bicyclic base structure B of formula II may have one or more ring double bonds and, in some instances, may have two or more ring double bonds. Preferably, the base structure has at least two double bonds and more preferably three or more double bonds.

Preferably the base structure B is selected form the following formulae (XI) to (XXI)

(XI)

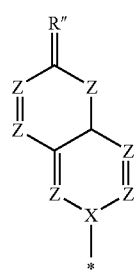 (XII)
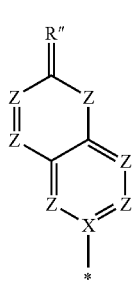 (XIII)
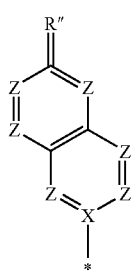 (XIV)
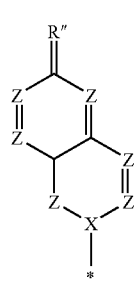 (XV)
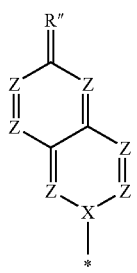 (XVI)
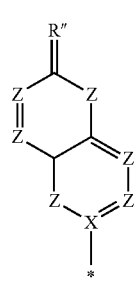 (XVII)
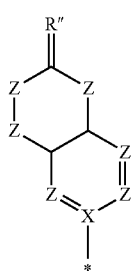 (XVIII)
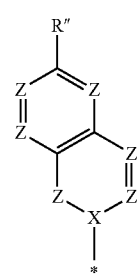 (XIX)
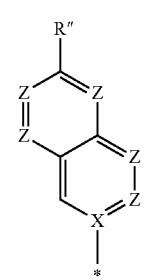 (XX)
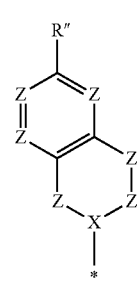 (XXI)
wherein Z, X and R″ are as defined above.

Examples of preferred base structures (B) are as follows:
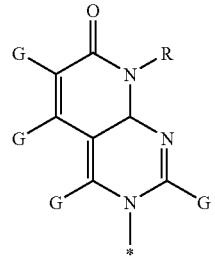
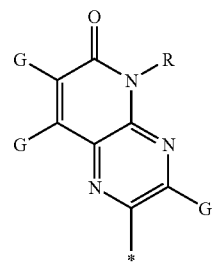
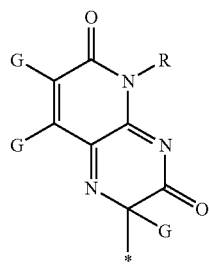
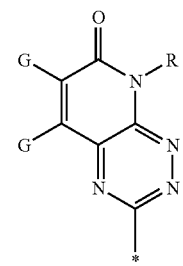
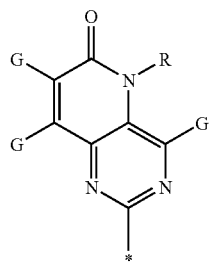
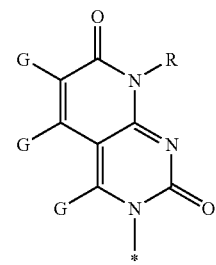
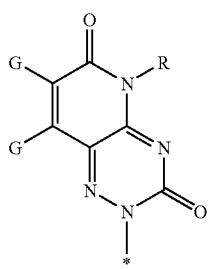
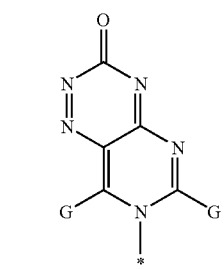
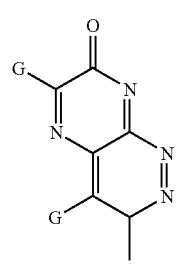
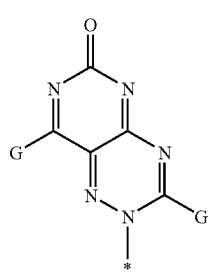
-continued
wherein G and R are as defined above.
Preferably X is N.
More preferably, the structure of formula II is represented by the structure of formula IIa
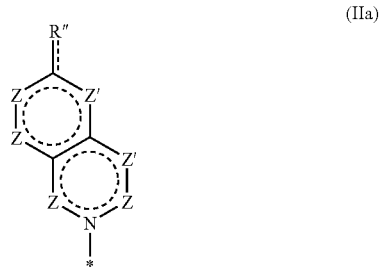
(IIa)
wherein each Z' is independently N (if a participant in a π bond) or NR (if not a participant in a π bond), and R", R and Z are as defined above.

Even more preferably, the structure of formula II is represented by the structure of formula IIb

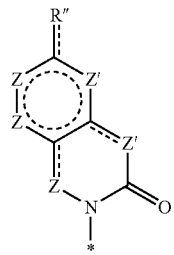
(IIb)

wherein R" and Z' are as defined above and each Z is independently CG (if a participant is π bond) or >C(G)$_2$ (if not a participant in a π bond).

Most preferably, the structure of formula II is represented by the structures of formulae IIC, IId and IIe

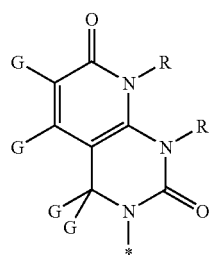
(IIc)

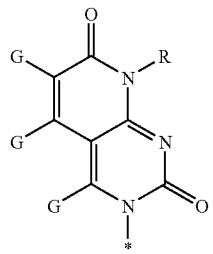
(IId)

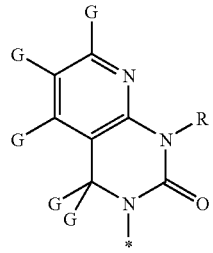
(IIe)

wherein R and G are as defined above.

Preferably, for the compounds of formulae IIc, IId and IIe each R is independently selected from H, optionally substituted alkyl, optionally substituted aryl, optionally substituted heteroaryl, optionally substituted heterocyclyl, and optionally substituted arylalkyl and each G is independently selected from H, halogen, CF$_3$, optionally substituted alkyl, optionally substituted aryl, optionally substituted heteroaryl, optionally substituted heterocyclyl, and optionally substituted arylalkyl.

In a further preferred embodiment L' is —CH$_2$—.

In yet a further preferred embodiment R$^{4'}$ is selected from —CH$_2$—OH, —CF$_2$OH, —CCl$_2$—OH, —C(CH$_3$)(CH$_3$)OH, —CH(CH$_3$)OH, —CH$_2$—CH$_2$—P(O)(OH)$_2$, —CH$_2$—CH$_2$—P(O)(OH)$_2$, —CH$_2$SP(O)(OH)$_2$, —CH$_2$SH, —CF$_2$SH, and —CH$_2$—O—P(O)(OPh)(NHCH(CH$_3$)(CO$_2$Me)).

More preferably R$^{4'}$ is —CH$_2$—OH.

Preferably, R$^1$, R$^2$, R$^{2'}$, R$^3$, R$^{3'}$, and R$^4$ are independently selected from the group consisting of H, halogen (more preferably F), OH, N$_3$, CN, optionally substituted alkyl, optionally substituted alkenyl, optionally substituted alkynyl, optionally substituted aryl, optionally substituted acyl, optionally substituted arylalkyl, optionally substituted heterocyclyl, optionally substituted heteroaryl, optionally substituted alkyloxy, optionally substituted acyloxy, optionally substituted oxyacyl, optionally substituted amino, optionally substituted aminoacyl, optionally substituted aminoacyloxy, optionally substituted acylamino, optionally substituted thio, or R$^2$ and R$^{2'}$ together or R$^3$ and R$^{3'}$ together represents =O, =S, or =L-Y' where L is N, CH, CF, CCl or CBr and Y' is H, halogen, N$_3$, methyl, ethyl or CN.

Even more preferably R$^1$, R$^2$, R$^{2'}$, R$^3$, R$^{3'}$, and R$^4$ are independently selected from the group consisting of H, F, Cl, Br, I, OH, SH, NH$_2$, NHOH, NHNH$_2$, N$_3$, COOH, CN, CONH$_2$, C(S)NH$_2$, COOR, R, OR, SR, SSR, NHR, and NR$_2$ wherein at least one of R$^2$ or R$^{2'}$ is a substituent other than H, and wherein R is selected from the group consisting of optionally substituted alkyl, optionally substituted alkenyl, optionally substituted alkynyl, optionally substituted aryl, optionally substituted acyl, and optionally substituted arylalkyl.

In yet another preferred embodiment, the sugar moiety is selected from the following formulae:

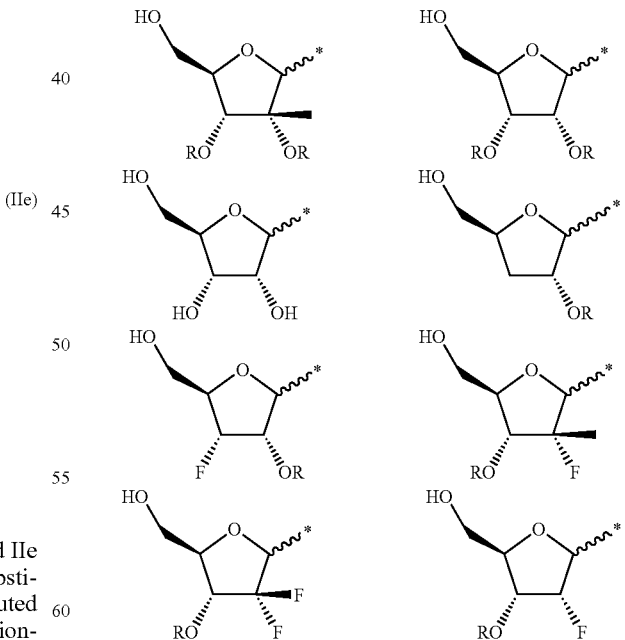

or C-5 monophosphate, diphosphate and triphosphate derivatives thereof, or C-5 mono, di or triphosphate mimics.

In another preferred embodiment, at least one of R$^2$ and R$^{2'}$ is methyl, hydroxyl or F.

More preferably, the sugar moiety is selected from the following formulae:

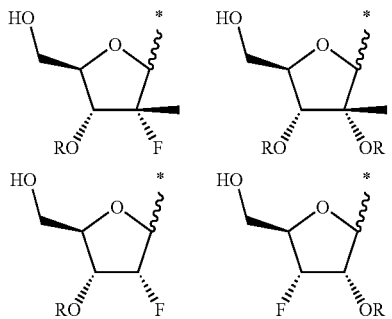

or C-5 monophosphate, diphosphate and triphosphate derivatives thereof, or C-5 mono, di or triphosphate mimics.

Accordingly, in a preferred embodiment the compound of formula (I) is selected from the following formulae, or salts thereof:

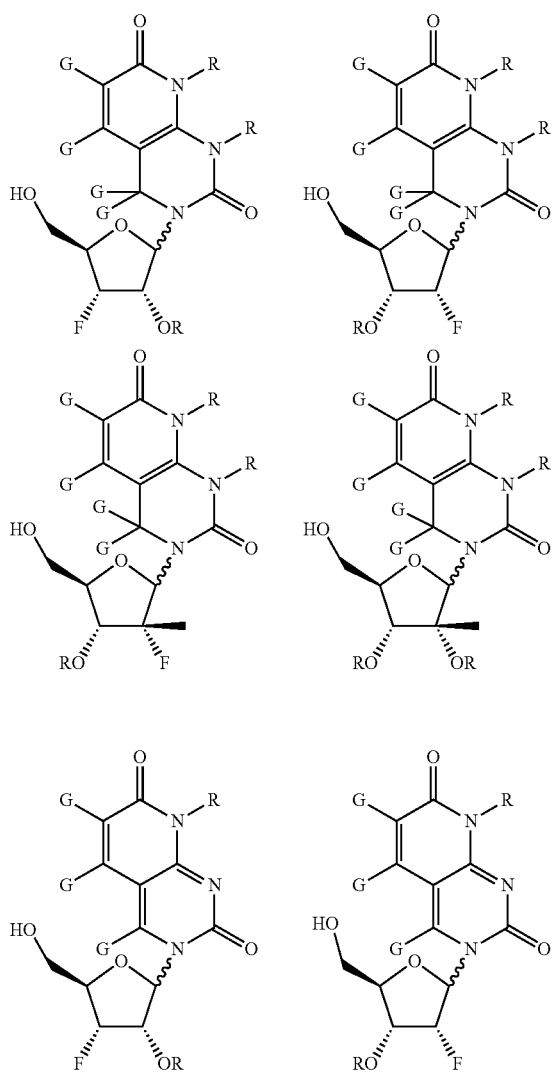

-continued

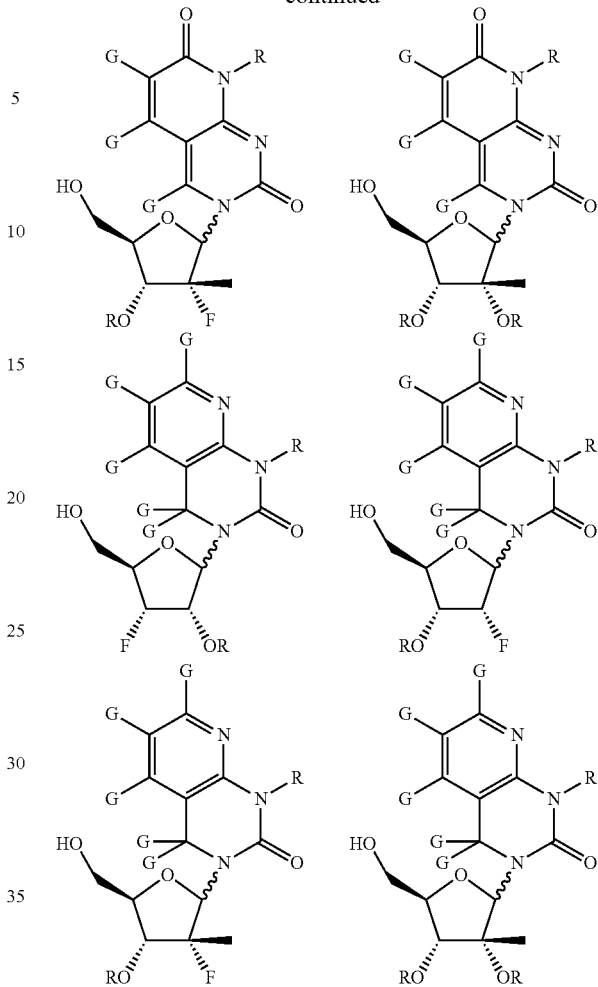

wherein:
each R on the sugar moiety is independently selected from H, optionally substituted alkyl, optionally substituted alkenyl, optionally substituted alkynyl, optionally substituted aryl, optionally substituted acyl and optionally substituted arylalkyl;

each R on the base moiety is independently selected from H, optionally substituted alkyl, optionally substituted aryl, optionally substituted heteroaryl, optionally substituted heterocyclyl, and optionally substituted arylalkyl;

each G is independently selected from H, halogen, $CF_3$, optionally substituted alkyl, optionally substituted aryl, optionally substituted heteroaryl, optionally substituted heterocyclyl, and optionally substituted arylalkyl; and C-5 monophosphate, diphosphate and triphosphate derivatives thereof, or C-5 mono, di or triphosphate mimics.

While nucleosides incorporating a variety of sugar moieties have been found to be useful for the inhibition of viral polymerases, in the case of the Flaviviridae, and in particular, the Hepatitis C virus, 2'-C-methyl ribnucleosides have been found to be particularly useful (see Eldrup, A. B. et al., J. Med. Chem. 2004, 47(21), 5284-97, which is incorporated herein by reference).

Accordingly, even more preferably, the sugar moiety is represented by the following formula:

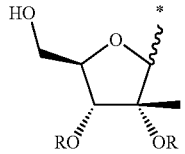

or C-5 monophosphate, diphosphate and triphosphate derivatives thereof, or C-5 mono, di or triphosphate mimics.

Most preferably, the sugar moiety is represented by the following formula:

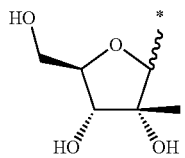

or C-5 monophosphate, diphosphate and triphosphate derivatives thereof, or C-5 mono, di or triphosphate mimics.

The bicyclic nucleosides of the present invention also include derivatives such as nucleotides, and nucleotide mimics and/or prodrugs thereof.

In some embodiments, nucleotide mimics of the compounds of the present invention of formula (I) discussed above include a compound in which $R^5$ is a monophosphate or monophosphate mimic of formula (XXII) or (XXIII):

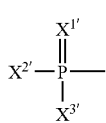
(XXII)

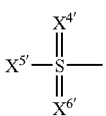
(XXIII)

where $X^{1'}, X^{4'}$, and $X^{6'}$, independently are O, S, NR; $X^{2'}, X^{3'}$, and $X^{5'}$ are selected independently from the group consisting of H, F, NROR, $N_3$, CN, $(BH_2G)^-M^+$, $(BH_3)^-M^+$, R, OR, SR, and $NR_2$. The substituents $(BH_2G)^-M^+$ and $(BH_3)^-M^+$ are ion pairs, which are linked to phosphorus through the negatively charged boron. $M^+$ is a cation, preferably a pharmaceutically acceptable cation such as $Ca^{2+}$, ammonium, trialkylammonium or tertaalkylammonium, e.g., $NH_4^+$, $Et_3NH^+$, $Bu_3NH^+$, and $Bu_4N^+$.

In some embodiments, nucleotide mimics of the compounds of formula (I) as discussed above include di- and triphosphates and di- and tri-phosphate mimics including a compound in which $R^5$ is a di- or tri-phosphate moiety of formula (XXIV):

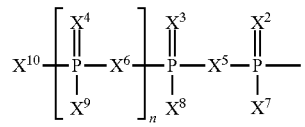
(XXIV)

$X^2$, $X^3$, and $X^4$ are selected independently from the group consisting of O, S, Se, and NR;

$X^5$ and $X^6$ are selected independently from the group consisting of —O—, —S—, —Se—, —CY$_2$C(O)—, —CH(OH)—, —C(OH)$_2$—, —CH$_2$O—, —CH$_2$CH$_2$—, —CH$_2$CH(NH$_2$)—, —CH$_2$CH$_2$CH(NH$_2$)—, —CY$_2$OCY$_2$—, —CY$_2$—, —CRY—, —CY$_2$CY$_2$—, —CHR—, —C≡C—, —HC=CH—, —NH—, —NR—, >NOH, >NOR, >NNH$_2$, and >NNHR;

$X^7$, $X^8$, $X^9$, and $X^{10}$ are selected independently from the group consisting of H, F, OR, SR, NR$_2$, NROR, NRNR$_2$, CN, N$_3$, $(BH_3)^-M^+$, $(BH_2G)^-M^+$, R and SeR;

Y, R, $(BH_2G)^-M^+$ and $(BH_3)^-M^+$ are as defined above; and n is 0 or 1.

Additional nucleotide phosphate mimics and methods of making the phosphate mimics appropriate for the compounds of the present invention are described, inter alia, in WO 2003/072757 and WO 2003/073989, the entire contents of which are incorporated herein by reference. Many of the nucleotide mimics discussed herein can be prepared by similar approaches as published or by using well-known knowledge of organophosphorous chemistry. Generally, phosphate mimics of the nucleosides and nucleotides of the present invention can inhibit enzyme function without phosphorylation and/or have enhanced nuclease stability relative to nucleotides with unmodified phosphate.

Accordingly, the term "phosphate mimic", unless otherwise specified, refers to a phosphate analog, including, but not limited to, phosphonate, phosphothiolate, phosphoselenoate, selenophosphate, thiophosphate, P-boranophosphate, phosphoramidate, sulfamate, sulfonate, and sulfonamide and/or a combination thereof. Preferred embodiments of the phosphate mimics include phosphonate, phosphoramidate, phosphorothioate, methylphosphonate, fluoromethylphosphonate, difluoromethylphosphonate, vinylphosphonate, phenylphosphonate, sulfonate, fluorophosphate, dithiophosphorothioate, 5'-methylenephosphonate, 5'-difluoromethylenephosphonate, 5'-deoxyphosphonate, 5'-aminophosphoramidate, and 5'-thiophosphate. More preferred is phosphonate and phosphoramidate.

Also, it will be appreciated that the term "diphosphate mimic" and "triphosphate mimic" specifically refer to a diphosphate analog and a triphosphate analog, respectively, which comprises at least one of the phosphate mimics, one of the modifications at the bridging site of diphosphate and triphosphate (eg. $X^5$, $X^6$ and $X^{10}$), and/or replacements of non-bridging phosphate oxygens (eg. $X^4$, $X^3$ and $X^2$).

The α-P, β-P, and γ-P in the mono, di- and triphosphate mimics may independently adopt either R or S configurations when chiral.

Accordingly, in compounds of formula (I) where a chiral centre is present, the invention encompasses enantiomers, or stereoisomers and mixtures thereof, such as enantiomerically enriched mixtures. It will also be appreciated that the base moieties of the present invention may exist as rapidly interconvertible mixtures of isomers. Isomerism of this kind is known in the art as tautomerism. Individual isomers are called tautomers. Where tautomerism is possible the present invention covers all possible tautomers of the compounds of formula (I).

The compounds of the present invention can be administered to a subject as a pharmaceutically acceptable salt thereof. It will be appreciated however that non-pharmaceutically acceptable salts also fall within the scope of the present invention since these may be useful as intermediates in the preparation of pharmaceutically acceptable salts.

Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benzenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In particular, the present invention includes within its scope cationic salts eg sodium or potassium salts, or alkyl esters (eg methyl, ethyl) of the phosphate group.

Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

In some embodiments, the bicyclic nucleosides and nucleotides of the present invention also include their prodrug derivatives. The term "prodrug" is used in its broadest sense and encompasses those derivatives that are converted in vivo to the compounds of the invention. Prodrugs of the compounds of the present invention may be prepared by modification of the sugar moiety or of the phosphate or phosphate mimic to include a prodrug substituent. Such prodrug modification is generally performed to enhance drug absorption and/or drug delivery into cells.

Prodrugs substituents include, but are not limited to residues of: proteins; antibiotics; D- and L-amino acids which may be attached to a phosphate moiety or a phosphate mimic moiety via a carbon atom (phosphonates), a nitrogen atom (phosphoamidates), or an oxygen atom (phosphoesters) or may be attached to the sugar moiety through any one or more of the $R^1$-$R^5$ groups; peptides (preferably up to 10 amino acids) attached to a phosphate moiety or a phosphate mimic moiety via a carbon atom (phosphonates), a nitrogen atom (phosphoamidates), or an oxygen atom (phosphoesters), or may be attached to the sugar moiety through any one or more of the $R^1$-$R^5$ groups; drug moieties attached to a phosphate moiety or a phosphate mimic moiety via a carbon atom (phosphonates), a nitrogen atom (phosphoamidates), or an oxygen atom (phosphoesters), or may be attached to the sugar moiety through any one or more of the $R^1$-$R^5$ groups; as well as including steroids; vitamins; polyamines; carbohydrates; polyethylene glycols (PEGs); cyclosaligenyls; substituted 4 to 8-membered rings, with or without heteroatom substitutions, 1,3-phosphoamidate attachments to a terminal phosphate or phosphate mimic moiety ($\gamma$ or $\beta$) or connecting between an $\alpha,\beta$ or $\beta,\gamma$ of a phosphate moiety or phosphate mimic moiety, and so on.

In addition to those described herein, prodrug derivatives of nucleosides, nucleotides and nucleotide phosphate mimics and methods of making the prodrugs appropriate for use in the present invention are described, inter alia, in PCT Publications WO 2003/072757 and WO 2003/073989.

The prodrug of a nucleoside 5'-monophosphate mimic can mask the negative charges of the phosphate mimic moiety entirely or partially, or mask the negative charges of the di-phosphate mimic or tri-phosphate mimic moiety or phosphate moiety in order to enhance drug absorption and/or drug delivery into cells.

In one embodiment a combination of prodrug substituents may be attached to one or more $X^{2'}$, $X^{3'}$ and $X^{5'}$ positions on a nucleoside mono-phosphate mimic or to one or more $X^7$—$X^{10}$ positions on a nucleoside di- or tri-phosphate mimic. Preferred prodrug substituents in positions $X^{2'}$, $X^{3'}$ or $X^{5'}$ position include 2,3-O-diacylglyceryloxy, 2,3-O-dialkylglyceryloxy, 1-O-alkyl-2-O-acylglyceryloxy, 1-O-acyl-2-O-alkylglyceryloxy, 1-S-alkyl-2-O-acyl-1-thioglyceryloxy, acyloxymethoxy, S-acyl-2-thioethoxy, S-pivaloyl-2-thioethoxy, acyloxymethoxy, pivaloyloxymethoxy, alkoxycarbonyloxymethoxy, S-alkyldithio-S'-ethyoxy acyloxymethoxy, S-acyl-2-thioethoxy, S-pivaloyl-2-thioethoxy, pivaloyloxymethoxy, alkoxycarbonyloxymethoxy, and S-alkyldithio-S'-ethyoxy.

In a further embodiment, the prodrug substituent is a substituent on a hydroxyl group of the sugar moiety (that is, for instance, any one of $R^1$-$R^5$). Preferably, the modification results in the formation of an ester and in this regard the preferred prodrug substituents are $C_1$-$C_6$acyl groups for example, acetyl, propionyl, pivaloyl, etc. Also preferred are substituted $C_1$-$C_6$ acyl moieties, for example, fluoroacetyl, difluoroacetyl, etc. More preferably the substituted $C_1$-$C_6$ acyl group is represented as a residue of a L or D amino acid consisting of alanine, asparagine, cysteine, glutamine, glycine, isoleucine, leucine, methionine, phenylalanine, proline, serine, threonine, tryptophan, tyrosine, valine, aspartic acid, glutamic acid, arginine, histidine, and lysine. Most preferably the prodrug substituent is an amino acid residue of D or L-valine.

The prodrug can be activated either by cellular enzymes such as lipases, esterases, reductases, oxidases, nucleases or by chemical cleavage such as hydrolysis to release (liberate) either the nucleoside, nucleotide or nucleotide mimic after the prodrug enters cells.

In addition to using prodrug approaches, the delivery of the nucleosides and nucleotides may be assisted by using a therapeutically acceptable carrier such as liposomal suspensions, cationic lipids, and polyimines.

The novel nucleosides, nucleotides, nucleotide mimics and prodrugs thereof, of the present invention can be prepared by those who are skilful in synthetic organic and nucleoside chemistry using established synthetic methodology (*Chemistry of Nucleosides and Nucleotides* Vol. 1 (1988), Vol. 2 (1991), Vol. 3 (1994), edited by L. B. Townsend, Plenum Press; *Handbook of Nucleoside Synthesis* by H. Vorbrüggen and C. Ruh-Pohlenz, John Wiley & Sons, Inc., 2001; *The Organic Chemistry of Nucleic Acids* by Y. Mizuno, Elsevier, 1986).

The nucleosides of the present invention can be converted to their corresponding monophosphate, diphosphate, and triphosphate nucleosides by established phosphorylation procedures. Similarly, known methods in the art can be used to synthesise the nucleotide and phosphate mimics and prodrugs. The following schemes and description serve as representative syntheses of the nucleosides and nucleotides of the present invention. As such, other compounds such as those having —$CY_2SH$, —$CY_2OH$ or -L'-$R^5$ groups other than $CH_2R^5$ may similarly be made.

The bicyclic nucleosides of the present invention may be prepared by modification of optionally protected and functionalised cytosine, uracil and other base analogues followed by Stille, Heck, Sonogashira or other metal-mediated cross coupling chemistry to introduce an α,β-unsaturated ester, alkyne or other functional group. Such processes allow for stereoselective synthesis of an intermediate capable of efficient cyclisation to form the bicyclic compounds of the present invention. Cyclisation and optional deprotection of the product delivers the target bicyclic nucleoside.

Any compound capable of metal-mediated cross coupling may be used, such as a tin derivative like trialkyltin. More preferably tributyltin. Preferably the reactions are carried out using a palladium based coupling agent. Suitable coupling agents are known in the art and include $Pd(PPh_3)_2Cl_2$, $Pd(PPh_3)_4$, Pd(dibenzylideneacetone), and $PdCl_2(CH_3CN)_2$. Also, preferably the palladium catalysed coupling reactions may also include a co-catalyst, for instance, CuI which may be in the presence of a suitable non-nucleophilic base such as a trialkylamine.

Coupling reactions are generally performed at temperatures around room temperature. Elevated temperatures such as temperatures between 30-80° C. can be employed to effect coupling and cyclisation in a single step. It is also preferred that such reactions are carried out under an inert atmosphere of either nitrogen or argon. Suitable solvents include ether solvents such as THF and diethylether or polar solvents such as DMF.

For example, Schemes 1 and 2 illustrates some preferred cyclisation methods for forming the 6-membered ring portions of the bicyclic bases (B) of the compounds of the present invention.

Scheme 1

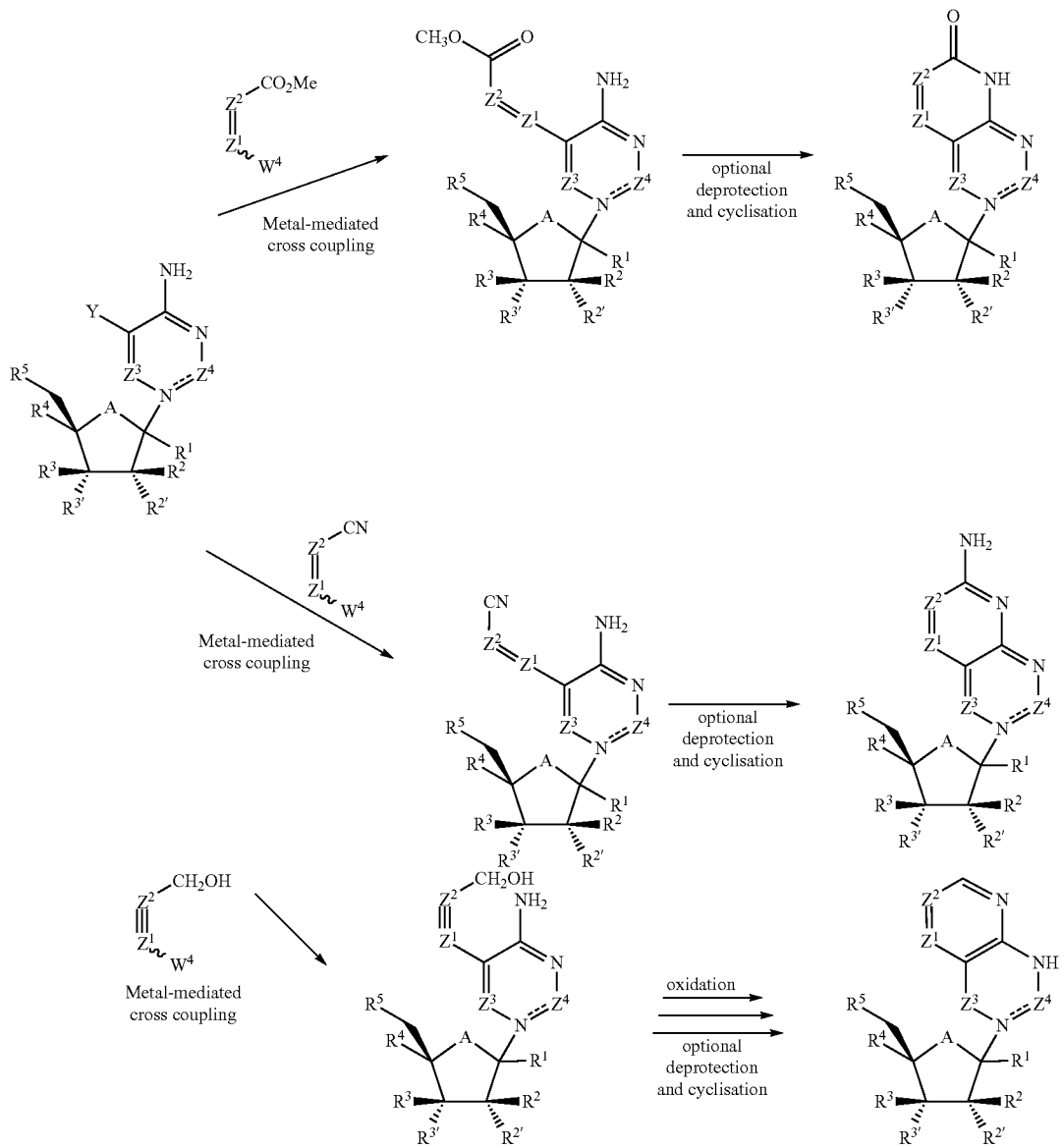

Methodologies other than metal-mediated cross-coupling and cyclisation can also be used to prepare the bicyclic nucleosides. For example, the final process in scheme 2 depicts how a bifunctional two atom unit (such as an α-halo-carboxylic ester or glyoxal) can be used to form the second 6-membered ring portion of a suitable nucleoside intermediate.

C-heteroaryl, C—O-alkyl or C—S-alkyl; $Z^3$ is CH, C-alkyl, C-halogen, N, CNHR, $CNH_2$, $CNR_2$, C=O, or C=S; $Z^4$ is CH, C-halogen, C-alkyl, C-aryl, C-heteroaryl, C—O-alkyl, C—S-alkyl, C—OH, C—$NH_2$, C—NHR, C—$NR_2$ or C=O; $R^1$, $R^2$, $R^{2'}R^3$, $R^{3'}$, $R^4$ are each independently H, halogen,

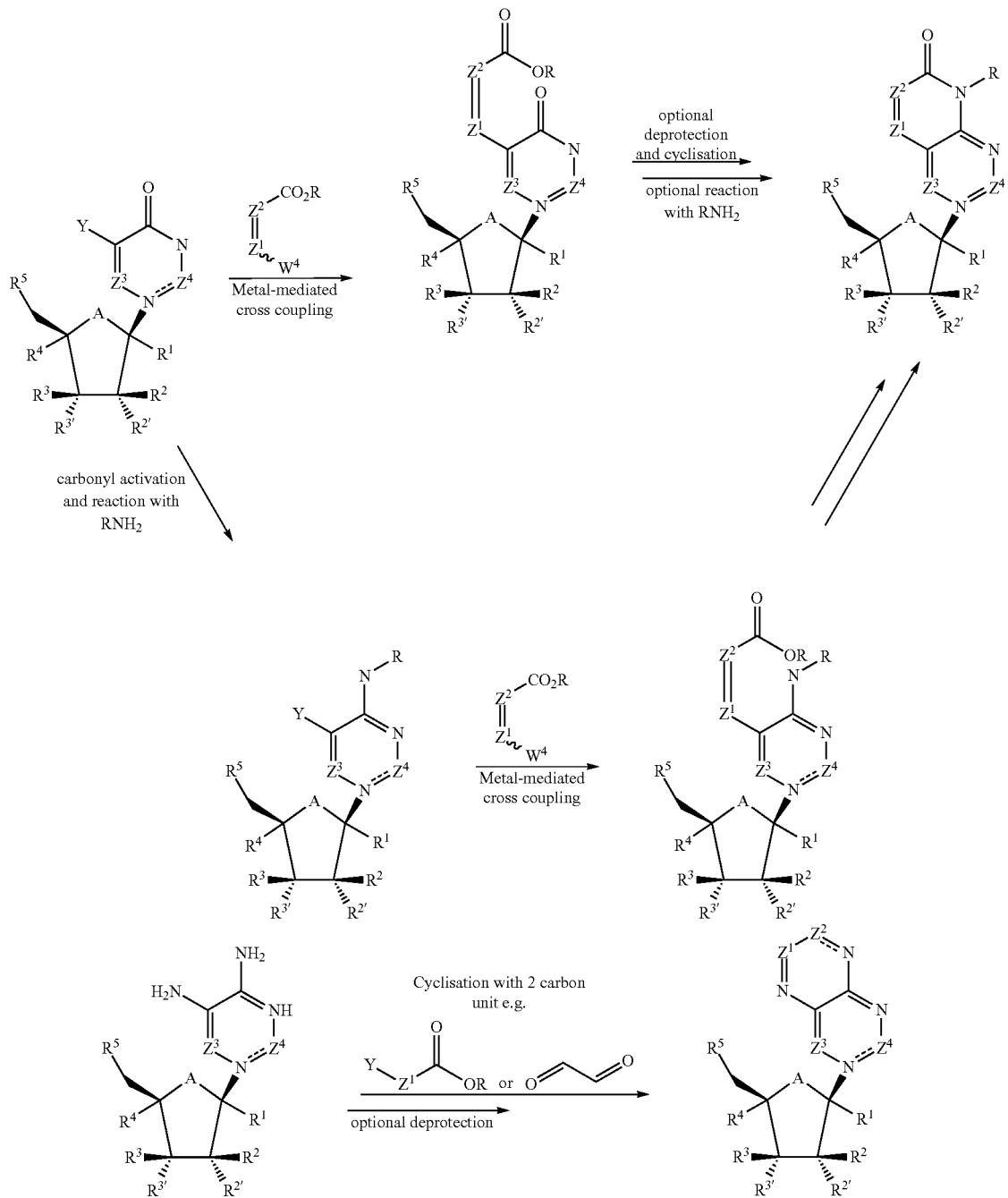

Scheme 2

In the cyclisation methodology depicted in Schemes 1 and 2 each of $Z^1$-$Z^4$ is independently Z.

Preferably, in this process A is O, $CH_2$ or optionally protected N; Y is halogen or other appropriate group such as trifluoromethanesulfonate; $W^4$ is H or trialkyltin; $Z^1$ and $Z^2$ are each independently C, CH, C-halogen, C-alkyl, C-aryl, C-heteroaryl, C—O-alkyl or C—S-alkyl; alkyl, O-alkyl, OH, optionally protected O, methyl, H or F; and $R^5$ is an optionally protected OH or $NH_2$; and (- -) denotes an optional double bond.

The bicyclic bases of the present invention can be further modified either prior to being added to the sugar moiety or once attached. Such modification may involve transformations through functionalisation, defunctionalisation, or functional group interconversion. Modifications may include esterification, the preparation of enol ethers, o-alkylation, bromination, hydrogenation, dihydroxylation, epoxidation, oximation, and amination.

The compounds described herein can also be converted into their corresponding mono-, di- and triphosphates using well established methods. Furthermore, as discussed above prodrugs of mono-, di- and triphosphates can be prepared in order to optimise the biological efficacy of these phosphorylated compounds. Methods for preparing such prodrugs are well known in the art (see Wagner, C. R., et al. *Med, Res. Rev.*, 2000, 20, 417-451).

Antiviral assays are conducted according to published, widely used protocols. In order to obtain the therapeutic index, compound-induced cytotoxicity to host cells is also measured in parallel with antiviral activities. To determine the mode of action of antiviral nucleosides the corresponding nucleoside triphosphates are subject to enzyme-based assays for the inhibition of viral polymerases according to known protocols (Ranjith-Kumar et al. *J. Virol.* 2001, 75, 8615; Dhanak et al. *J. Biol. Chem.* 2002, 277, 38322-38327). Some compounds of the present invention showed $K_i$ values of less than 1 μM against HCV NS5B.

Since the replicon RNA replication mimics the replication of HCV RNA in infected hepatocytes, compounds that have the inhibitory effects in replicon assays are potentially useful

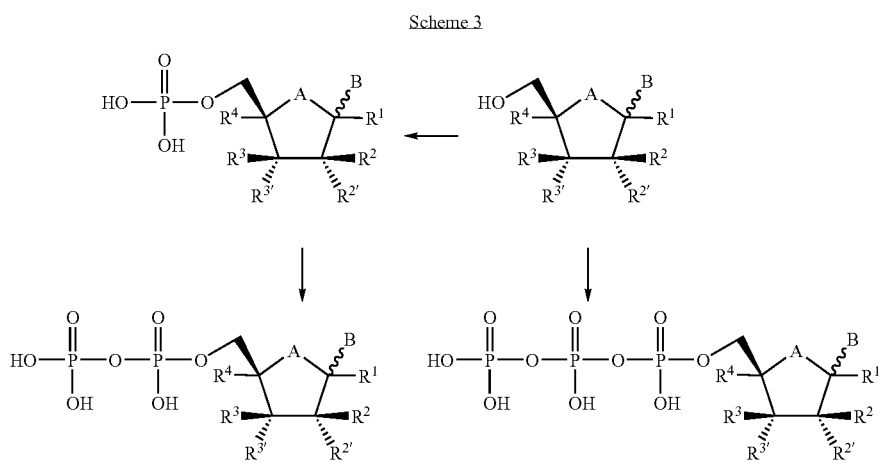

Scheme 3

In Scheme 3, preferably A is O, $CH_2$ or optionally protected N; $R^1$, $R^2$, $R^{2'}$, $R^3$, $R^{3'}$, $R^4$ are each independently H, halogen, alkyl, O-alkyl, OH, optionally protected O, or methyl and B is as described herein.

As discussed earlier an alternative to the use of phosphates is the use of phosphate mimics and their prodrugs. One such phosphate mimic is shown below and this can be prepared using appropriately protected nucleosides and known conditions.

as anti-HCV drugs. The HCV replicon-containing cell lines (Randall and Rice, *Current Opinion in Infectious Diseases* 2001, 14, 743) are used for the identification of potential anti-HCV compounds. Among them is a widely used subgenomic replicon system developed by Lohmann et al. (*Science* 1999, 285, 110; *J. General Virol.* 2000, 81, 1631; *J. Virol.* 2001, 75, 1437, 2002, 76, 4008). Some compounds of the present invention showed potent anti-HCV activity with $EC_{50}$ values of low μM.

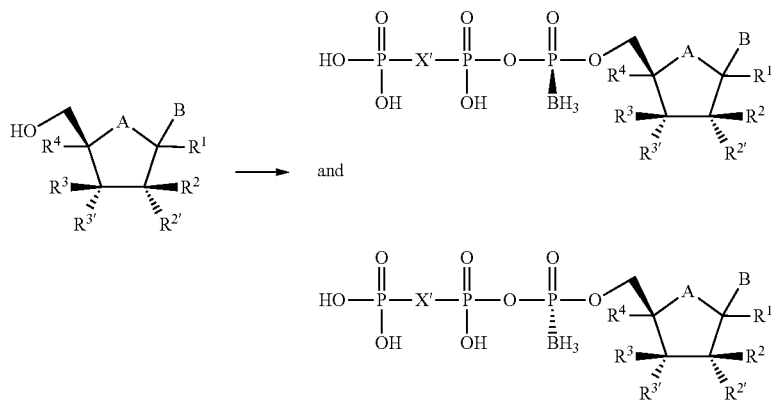

In Scheme 4, preferably A is O, $CH_2$ or optionally protected N; $R^1$, $R^2$, $R^{2'}$, $R^3$, $R^{3'}$, $R^4$ are each independently H, halogen, alkyl, O-alkyl, OH, optionally protected O, methyl or F; X' is O, S, NH, $CF_2$, CHF, CClH, $CBr_2$ or CHBr; B is as described herein.

The bicyclic compounds of the present invention may be tested for biological activity using well known procedures.

Widely used protocols developed by Korba et al. (*Antiviral Res.* 1992, 19, 55), and Pai et al. (*Antimicrobial Agents Chemother.* 1996, 40, 380) are useful for the determination of in vitro anti-HBV activity.

Anti-HIV assays can be conducted according to the protocols developed by Schinazi et al. (*Antimiromobial Agents Chemother.* 1990, 34, 1061; 1992, 36, 2423; 1993, 37, 875) or other widely used protocols (Kimpton et al. *J. Virol.* 1992, 66, 2232; Chan et al. *J. Med. Chem.* 2001, 44, 1866).

Preferred nucleoside triphosphates of the present invention may act as potent inhibitors of the non-structural position 5B (NS5B) which is HCV's RNA-dependent RNA polymerase. Accordingly, such compounds are preferably suited to treat and/or prevent HCV. Also, as the preferred novel compounds of the present invention are expected to exhibit novel profiles of activity they may provide the artisan with an alternative to treating viruses which display drug resistance to conventional drugs. Other advantages which may be exhibited by the preferred novel compounds of the present invention include:
  reduced toxicity and tolerability relative to existing therapies and those in development; and/or
  improved pharmacokinetic properties.

Accordingly, nucleosides, nucleotide, nucleotide mimics and/or their prodrugs of the present invention may be useful for the inhibition of a variety of enzymes including, but not limited to, DNA or RNA polymerases, helicases, ribonucleotide reductases, protein kinases, and telomerases and for the modulation of G-proteins, P2 purinergic receptors and the allosteric sites of a variety of enzymes. Preferably, the novel nucleosides, nucleotides, nucleotide mimics and/or prodrugs of the present invention are used to treat viral infections caused by the RNV viruses of the group Flaviviridae and, in particular, HCV.

The novel nucleosides, nucleotides, nucleotide mimics and/or their prodrugs of the present invention are useful for the treatment of infectious diseases caused by infectious agents such as parasites, bacteria and fungi.

Also, the novel nucleosides, nucleotide mimics and/or their prodrugs that display potent cytotoxicities to fast-dividing cancerous cells may be useful for the treatment of proliferative disorders, including, but not limited to, lung cancer, liver cancer, prostate cancer, colon cancer, breast cancer, ovarian cancer, melanoma, and leukemia.

As the ligands of P2 receptors and G-proteins as well as the inhibitors of protein kinases, the novel nucleosides, nucleotides, nucleotide mimics and/or their prodrugs of the present invention may also be useful for the treatment of a wide range of other diseases and disorders such as inflammatory diseases, autoimmune diseases, Type 2 diabetes, and cardiovascular diseases.

In order to overcome drug resistance, combination therapies are widely used in the treatment of infectious diseases and proliferative disorders. The nucleosides, nucleotides, nucleotide mimics and/or their prodrugs of the present invention may be therapeutically administered as a single drug, or alternatively may be administered in combination with one or more other active chemical entities to form a combination therapy. The other active chemical entities may be a small molecule, a polypeptide, or a polynucleotide.

For instance, compounds of this invention may be particularly useful when used in combination with other agents known to exert an antiviral effect. For example, combination with immunomodulatory/antiviral agents such as interferons, interferon derivatives and other large or small molecules known to modulate host immune responses may be beneficial. Similarly, combinations of compounds of this invention with IMPDH inhibitors (e.g. ribavirin), antiviral nucleosides, antiviral non-nucleosides (e.g. polymerase inhibitors, protease inhibitors) could augment the activity of the bicyclic nucleosides when administered alone.

The following examples are put forth so as to provide those of ordinary skill in the art with a complete disclosure and description of how to prepare and use the compounds disclosed and claimed herein.

All references mentioned herein are incorporated herein by reference in their entirety.

The abbreviations that may be used herein, including the Schemes and experimental section are as follows unless indicated otherwise:
Bu: n-butyl
Bn benzyl
Bz: benzoyl
DCM: dichloromethane
DIEA: diisopropylethylamine
DMF: dimethylformamide
Et: ethyl
EtOAc: ethyl acetate
Me: methyl
MeOH: methyl alcohol
MS: mass spectrometry
NMR: nuclear magnetic resonance
Ph: phenyl
HPLC: high performance liquid chromatography
TEA: triethylamine
TFA: trifluoroacetic acid
THF: tetrahydrofuran The following Examples are offered to illustrate but not to limit the invention.

EXAMPLES

TABLE 1

Synthesis

| Example | Structure | Molec Formula | MWt |
|---|---|---|---|
| 1 | 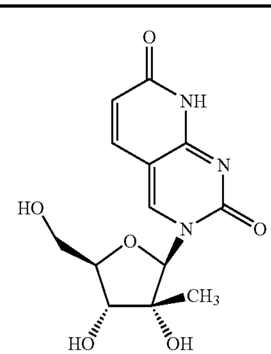 | $C_{13}H_{15}N_3O_6$ | 309.28 |

TABLE 1-continued

| Synthesis | | | |
|---|---|---|---|
| Example | Structure | Molec Formula | MWt |
| 2 | | $C_{13}H_{14}IN_3O_6$ | 435.17 |
| 3 | | $C_{13}H_{14}BrN_3O_6$ | 388.17 |
| 4 | | $C_{13}H_{14}ClN_3O_6$ | 343.72 |
| 5 | | $C_{13}H_{15}N_3O_6$ | 309.28 |

TABLE 1-continued

| Example | Structure | Molec Formula | MWt |
|---|---|---|---|
| 6 | 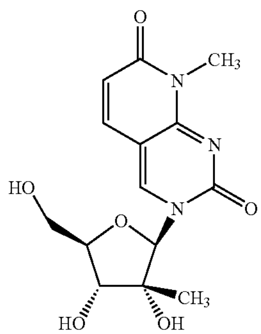 [SMILES: Cn1c(=O)ccc2cn([C@@H]3O[C@H](CO)[C@@H](O)[C@@]3(C)O)c(=O)nc21] | $C_{14}H_{17}N_3O_6$ | 323.30 |
| 7 | 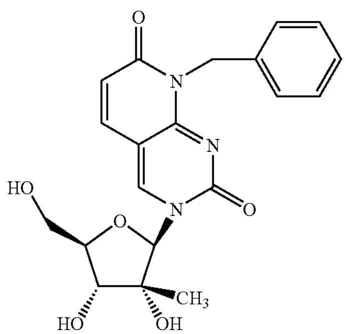 [SMILES: C[C@@]1(O)[C@H](O)[C@@H](CO)O[C@H]1n1cc2ccc(=O)n(Cc3ccccc3)c2nc1=O] | $C_{20}H_{21}N_3O_6$ | 399.40 |
| 8 | 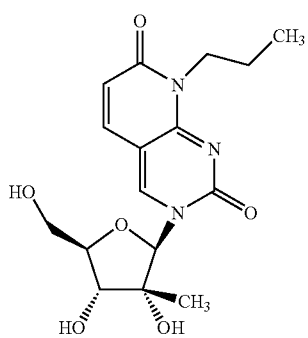 [SMILES: CCCn1c(=O)ccc2cn([C@@H]3O[C@H](CO)[C@@H](O)[C@@]3(C)O)c(=O)nc21] | $C_{16}H_{21}N_3O_6$ | 351.36 |
| 9 | 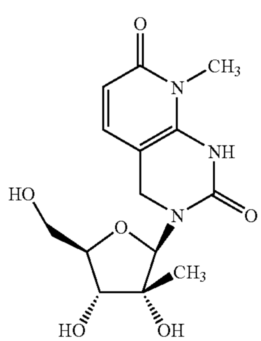 [SMILES: Cn1c2c(ccc1=O)CN([C@@H]1O[C@H](CO)[C@@H](O)[C@@]1(C)O)C(=O)N2] | $C_{14}H_{19}N_3O_6$ | 325.32 |

TABLE 1-continued

| Example | Structure | Molec Formula | MWt |
|---|---|---|---|
| 10 | 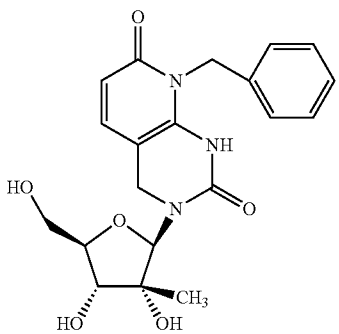 [SMILES: C[C@@]1(O)[C@H](O)[C@@H](CO)O[C@H]1N1Cc2ccc(=O)n(Cc3ccccc3)c2NC1=O] | $C_{20}H_{23}N_3O_6$ | 401.42 |
| 11 | 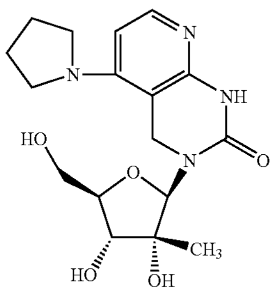 [SMILES: C[C@@]1(O)[C@H](O)[C@@H](CO)O[C@H]1N1Cc2c(N3CCCC3)ccnc2NC1=O] | $C_{17}H_{24}N_4O_5$ | 364.40 |
| 12 | 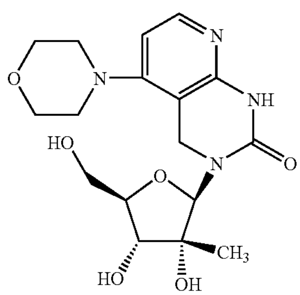 [SMILES: C[C@@]1(O)[C@H](O)[C@@H](CO)O[C@H]1N1Cc2c(N3CCOCC3)ccnc2NC1=O] | $C_{17}H_{24}N_4O_6$ | 380.40 |
| 13 | 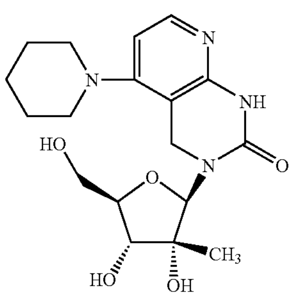 [SMILES: C[C@@]1(O)[C@H](O)[C@@H](CO)O[C@H]1N1Cc2c(N3CCCCC3)ccnc2NC1=O] | $C_{18}H_{26}N_4O_5$ | 378.43 |
| 14 | 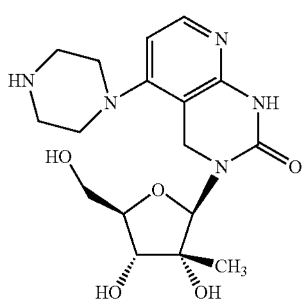 [SMILES: C[C@@]1(O)[C@H](O)[C@@H](CO)O[C@H]1N1Cc2c(N3CCNCC3)ccnc2NC1=O] | $C_{17}H_{25}N_5O_5$ | 379.41 |

TABLE 1-continued

Synthesis

| Example | Structure | Molec Formula | MWt |
|---|---|---|---|
| 15 | 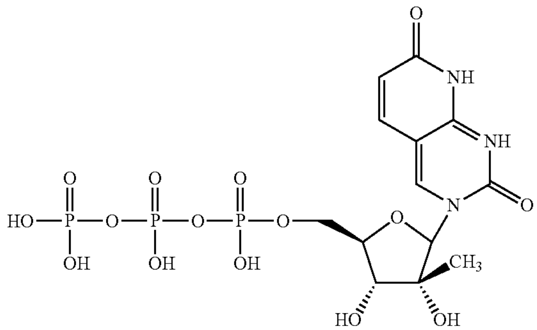 [SMILES: C[C@]1(O)C(n2cc3ccc(=O)[nH]c3nc2=O)O[C@H](COP(=O)(O)OP(=O)(O)OP(=O)(O)O)[C@H]1O] | $C_{13}H_{18}N_3O_{15}P_3$ | 549.21 |

Experimental Data $^1$H and $^{31}$P NMR spectra were recorded on either a Bruker Avance DRX 400, AC 200 or AM 300 spectrometer. Spectra were recorded in CDCl$_3$, d$_6$-acetone, CD$_3$OD or d$_6$-DMSO using the residual solvent peak as a reference. Chemical shifts are reported on the δ scale in parts per million (ppm) using the following conventions to assign the multiplicity: s (singlet), d (doublet), t (triplet), q (quartet), m (multiplet) and prefixed b (broad). Mass spectra (ESI) were recorded on a Finnigan LCQ Advantage spectrometer. All microwave reactions were carried out in a CEM Discover microwave reactor. Flash and radial chromatography was performed on 40-63 μm silica gel 60 (Merck No. 9385). Preparative HPLC was carried out using a Gilson 322 pump with a Gilson 215 liquid handler and a HP1100 PDA detector. HPLC systems employed Phenomonex C8(2) columns using either acetonitrile or acetonitrile containing 0.06% TFA in water or water containing 0.1% TFA. Alternatively, a Phenomonex C18 column was used with acetonitrile and aqueous 1M triethylammonium acetate (primarily for phosphate nucleotides).

Scheme 5

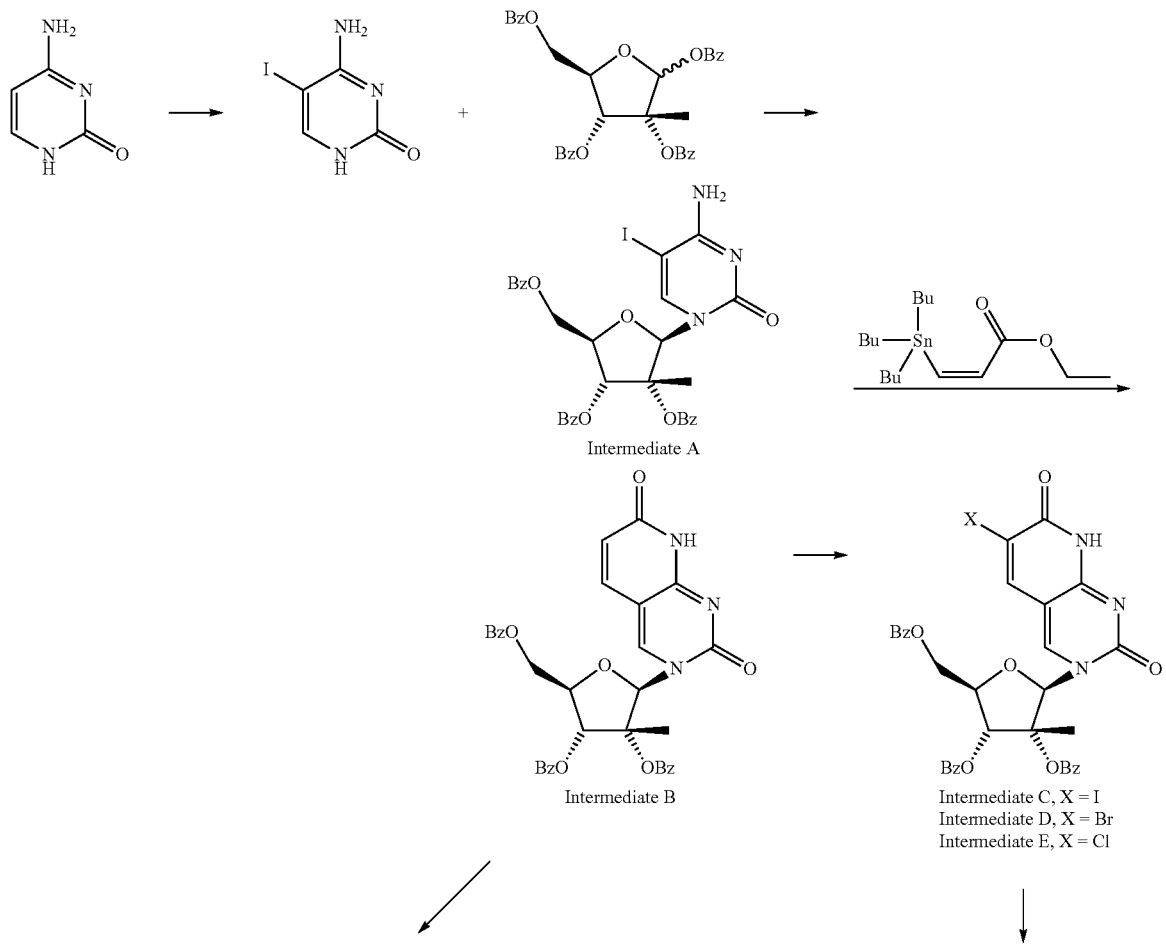

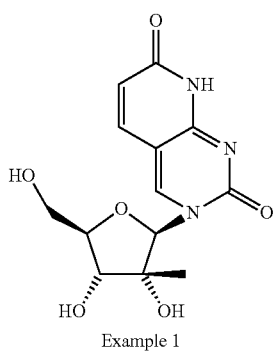

Example 1

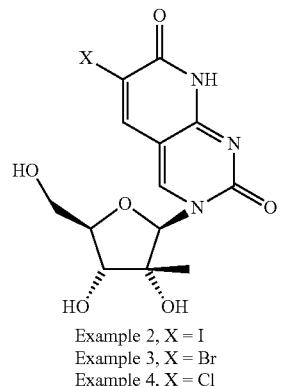

Example 2, X = I
Example 3, X = Br
Example 4, X = Cl

Intermediate A

N,O-Bis(trimethylsilyl)acetamide (7.17 mL) was added to 5-iodocytidine (2.32 g) in dry acetonitrile (15 mL) and the mixture was heated under argon at 80° C. for 30 mins. A suspension of commercially available 1,2,3,5-tetra-O-benzoyl-2-C-methyl-alpha/beta-D-ribofuranose (5.16 g) in dry acetonitrile (40 mL) was added and the mixture heated for 1 h. SnCl$_4$ (1.71 mL) was added cautiously and heating continued for 2 hrs. The reaction was cooled to ambient temperature, poured into an ice cold solution of saturated aqueous sodium bicarbonate and extracted with EtOAc (×3). The combined organic extracts were washed with brine, dried and evaporated in-vacuo. The residue was purified by flash chromatography on silica eluting with 3% MeOH/DCM. The product was obtained as a gum (3.36 g). MS m/z ([M+H]$^+$) 695.7; ([2M+H]$^+$) 1390.8.

Intermediate B

A degassed solution of intermediate A (1.39 g) and (Z)-ethyl-3-(tributylstannyl) propenoate (1.56 g) was stirred in dry DMF under argon for 10 mins. CuI (76 mg) and PdCl$_2$(PPh$_3$)$_2$ (140 mg) were added and the mixture heated at 70° C. under argon for 16 hrs. The reaction was cooled to ambient temperature, diluted with water (100 mL) and filtered. The residue was washed with water, dissolved in EtOAc and washed again with water. The organic solution was dried (MgSO$_4$) and the solvent evaporated in-vacuo to provide a brown gum. The aqueous mother liquor was also extracted with EtOAc (×2) and the combined organics dried (MgSO$_4$), and evaporated in-vacuo. The combined crude extracts were purified by radial chromatography on silica eluting with 3%-5% MeOH/DCM to give the required product as an oil, which, on trituration with ether afforded a yellow crystalline solid (70 mg). MS m/z ([2M+H]$^+$) 1243.5. Further product was available from the mother-liquor.

Preparation of Intermediates C, D, E

Preparation of Intermediate C is an Example of the General Method.

A mixture of Intermediate B (125 mg) and N-iodosuccinimide (90.6 mg) in dry acetonitrile (1.50 mL) was heated in a microwave reactor at 120° C. for 30 mins (initial power 200 W). The solution was evaporated in-vacuo, dissolved in EtOAc and washed with 10% sodium metabisulphite, brine, and evaporated in-vacuo. The crude material was purified by radial chromatography on silica eluting with 3% MeOH/DCM to yield the required product (120 mg). MS m/z ([2M+H]$^+$) 1494.3.

Similarly for Intermediates D and E.

Intermediate D

Intermediate B (62 mg) yielded intermediate D (45 mg). MS m/z ([2M+H]$^+$) 1400.6, 1401.6, 1403.6.

Intermediate E

Intermediate B (62 mg) yielded 62 mg intermediate D. MS m/z ([2M+H]$^+$) 1310.6, 1311.7, 1313.7.

Preparation of Examples 1-4

Preparation of Example 1 is an example of the general method.

Example 1

Intermediate B (60 mg) was suspended in dry methanol (1 mL) under argon. A freshly prepared solution of 1M sodium methoxide in methanol (0.5 mL) was added and the reaction stirred for 18 hrs. Evaporation of the solvent in-vacuo with minimal heating and purification by radial chromatography on silica eluting with 20% MeOH/DCM yielded the required compound as a crystalline solid.

MS m/z ([M+H]$^+$) 309.9. 1H $^1$H NMR (CD$_3$OD+D$_2$O) δ 9.24 (s, 1H), 7.61 (d, 1H), 6.23 (d, 1H), 6.11 (s, 1H), 4.08-4.00 (m, 2H), 3.93-3.83 (m, 2H), 1.12 (s, 3H).

Similarly for Examples 2 and 3.

Example 2

Intermediate C (12 mg) yielded Example 2 (1.70 mg)
MS m/z ([M+H]$^+$) 435.7, ([2M+H]$^+$) 870.4. $^1$H NMR (CD$_3$OD) δ 9.26 (s, 1H), 8.18 (s, 1H), 6.10 (s, 1H), 4.07-4.00 (m, 2H), 3.95-3.82 (m, 2H), 1.12 (s, 3H).

Example 3

Intermediate D (21 mg) yielded Example 3 (4.1 mg)
MS m/z ([M+H]$^+$) 387.7, 389.7. $^1$H NMR (CD$_3$OD) δ 9.28 (s, 1H), 7.95 (s, 1H), 6.10 (s, 1H), 4.07-3.99 (m, 2H), 3.89-3.82 (m, 2H), 1.12 (s, 3H).

Example 4

Intermediate E (28 mg) was stirred with 7M NH₃ in MeOH at ambient temperature for 18 h. The reaction was evaporated to dryness in-vacuo, dissolved in water (2 mL) and washed with DCM (×3) and EtOAc. The aqueous phase was evaporated and the residue triturated with ether to yield the required compound as a yellow solid (12 mg).

MS m/z ([M+H]$^+$) 343.7, 345.7; ([2M+H]$^+$) 686.6, 688.6. $^1$H NMR (CD$_3$OD) δ 9.34 (s, 1H), 7.73 (s, 1H), 6.11 (s, 1H), 4.07-3.99 (m, 2H), 3.90-3.82 (m, 2H), 1.12 (s, 3H).

Example 5

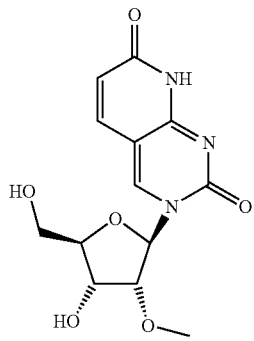

Example 5 (10.5 mg) was prepared directly from commercially available 5-Iodo-2'-O-methylcytidine using the method described for intermediate B in scheme 1.

MS m/z ([M+H]$^+$) 309.8; ([2M+H]$^+$) 618.6, ([2M+Na]$^+$) 640.8. $^1$H NMR (CD$_3$OD+D$_2$O) δ 9.23 (s, 1H), 7.64 (d, 1H), 6.27 (d, 1H), 5.95 (s, 1H), 4.21-4.17 (m, 1H) 4.06-4.02 (m, 2H), 3.95-3.73 (m, 2H), 3.64 (s, 3H).

Scheme 6

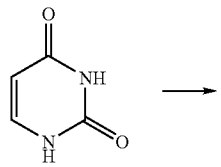

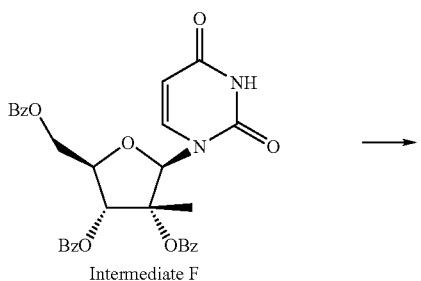
Intermediate F

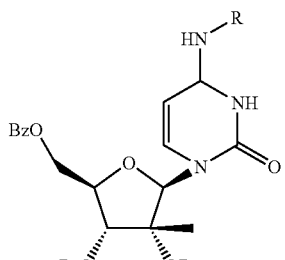
Intermediate G, R = Me
Intermediate H, R = Bn
Intermediate I, R = nPr

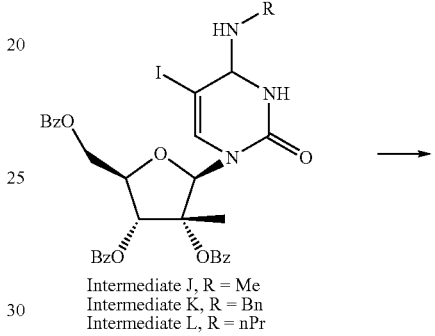
Intermediate J, R = Me
Intermediate K, R = Bn
Intermediate L, R = nPr

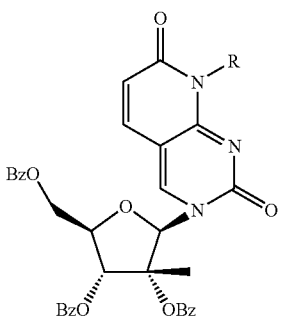
Intermediate M, R = Me
Intermediate N, R = Bn
Intermediate O, R = nPr

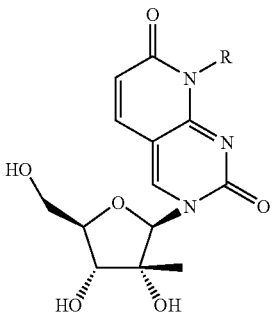
Example 6, R = Me
Example 7, R = Bn
Example 8, R = nPr

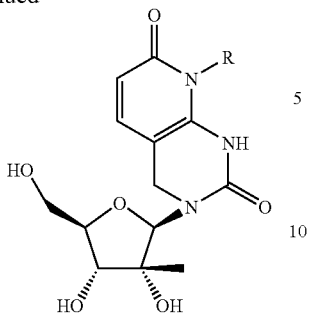

Example 9, R = Me
Example 10, R = Bn

Intermediate F

N,O-Bis(trimethylsilyl)acetamide (6.45 mL) and uracil (0.986 g) in dry acetonitrile (20 mL) were heated under argon at 80° C. for 30 mins. A suspension of commercially available 1,2,3,5-tetra-O-benzoyl-2-C-methyl-alpha/beta-D-ribofuranose in dry acetonitrile (80 mL) was added and heating continued for 1 hr. SnCl$_4$ was added cautiously and heating continued for 5 hrs. The reaction was cooled to ambient temperature, poured into an ice cold solution of saturated sodium bicarbonate (100 mL) and extracted with EtOAc (×3). The combined organic extracts were washed with brine, dried (MgSO$_4$) and evaporated in-vacuo to provide crude product as a frothy white gum (4.7 g) which was used in subsequent reactions without further purification. MS m/z ([M+H]$^+$) 571, ([2M+Na]+) 1163.

Intermediate G 1,2,4-triazole (207 mg) was dissolved in dry acetonitrile (5 mL) under argon, cooled to 0° C. and treated with POCl$_3$ (75 µL). After 5 mins, triethylamine (0.60 mL) was added and stirring continued for 1 h at ambient temperature before addition of Intermediate F in dry acetonitrile (5 mL). The reaction was diluted with EtOAc after 90 mins and washed successively with saturated NaHCO$_3$ and brine (each ×3). The organic layer was dried (MgSO$_4$) and evaporated in-vacuo to provide the crude triazole intermediate as a yellow gum (127 mg). This gum was suspended in MeOH (5 mL) and 2M MeNH$_2$ in MeOH (0.20 mL) added followed by vigorous stirring for 20 mins. After this time, volatile materials were evaporated in-vacuo and the residue purified by radial chromatography on silica eluting with 2% MeOH/DCM to give the required product as a gum (46 mg). MS m/z ([M+H]$^+$) 583.9, ([2M+H]$^+$) 1166.9.

Intermediate H

The crude triazole intermediate (621 mg) was prepared using the method described for intermediate G. This gum was suspended in dry ethanol (10 mL) before addition of benzylamine (164 µl). After stirring for 1 hr at ambient temperature the solvent was removed in-vacuo and the residue purified by radial chromatography on silica eluting with 3%-5% MeOH/DCM to give the required product as an oil (424 mg). MS m/z ([M+H]$^+$) 660.4, 661.4.

Intermediate I

The crude triazole intermediate (249 mg) was prepared using the method described for intermediate G. This gum was suspended in dry methanol (5 mL) before addition of N-propylamine (49 µl). After stirring for 30 mins at ambient temperature the solvent was removed in-vacuo and the residue purified by radial chromatography on silica eluting with 3% MeOH/DCM to give the required product as gum (45 mg). MS m/z ([M+H]$^+$) 612.4, 613.4.

Intermediates J, K and L were prepared by the general method described previously for Intermediate C.

Intermediate J

Intermediate G (200 mg) yielded Intermediate J (87 mg) MS m/z ([M+H]$^+$) 709.7.

Intermediate K

Intermediate H (188 mg) yielded Intermediate K (110 mg). MS m/z ([M+H]$^+$) 785.9.

Intermediate L

Intermediate I (130 mg) yielded Intermediate L (106 mg). MS m/z ([M+H]$^+$) 738.2

Intermediates M, N and O were prepared by the general method described previously for Intermediate B.

Intermediate M

A degassed solution of intermediate J (100 mg) and (Z)-ethyl-3-(tributylstannyl) propenoate (110 mg) was stirred in dry DMF under argon for 10 mins. CuI (5.5 mg) and PdCl$_2$(PPh$_3$)$_2$ (10 mg) were added and the mixture heated at 70° C. under argon for 16 hr. The solvent was evaporated in-vacuo and the residue partitioned between EtOAc and water. The aqueous phase was further extracted with EtOAc (×2) and the combined organic extracts dried (MgSO$_4$) and evaporated in-vacuo. The crude product was purified by radial chromatography on silica eluting with 3% MeOH/DCM to provide a yellow gum (56 mg).

MS m/z ([M+H]$^+$) 635.8, ([2M+H]$^+$) 1270.7.

Intermediate N

Intermediate K (120 mg) yielded Intermediate N (19 mg). MS m/z ([M+H]$^+$) 711.7, ([2M+H]$^+$) 1422.5.

Intermediate O

Intermediate L (105 mg) yielded Intermediate O (19 mg). MS m/z ([M+H]$^+$) 663.9, ([2M+H]$^+$) 1326.9.

Example 6

Intermediate M (36 mg) was stirred with 7M NH$_3$ in MeOH (3 mL) at ambient temperature for 4 hrs. The reaction was evaporated to dryness in-vacuo and the residue purified by radial chromatography on silica eluting with DCM/MeOH/25% NH$_3$ 90:9:1 to yield the required compound as a yellow solid (6 mg).

MS m/z ([M+H]$^+$) 323.8. 1H $^1$H NMR (CD$_3$OD) δ 9.28 (s, 1H), 7.51 (d, 1H), 6.33 (d, 1H), 6.12 (s, 1H), 4.08-3.99 (m, 2H), 3.91-3.86 (m, 2H), 3.53 (s, 3H), 1.12 (s, 3H).

Similarly for Examples 7 and 8.

Example 7

Intermediate N (19 mg) yielded Example 7 (3.9 mg).
MS m/z ([M+H]$^+$) 399.9. 1H $^1$H NMR (CD$_3$OD) δ 9.30 (s, 1H), 7.54 (d, 1H), 7.40-7.35 (m, 2H), 7.26-7.17 (m, 3H), 6.36 (d, 1H), 6.12 (s, 1H), 5.44 (s, 1H), 4.07-3.99 (m, 2H), 3.91-3.81 (m, 2H), 1.12 (s, 3H).

Example 8

Intermediate O (38 mg) yielded Example 8 (8.0 mg).
MS m/z ([M+H]$^+$) 351.8. 1H $^1$H NMR (CD$_3$OD) δ 9.30 (s, 1H), 7.50 (d, 1H), 6.32 (d, 1H), 6.12 (s, 1H), 4.21-4.16 (m, 2H), 4.08-3.99 (m, 2H), 3.91-3.83 (m, 2H), 1.74-1.61 (m, 2H), 1.12 (s, 3H), 0.93 (t, 3H).

Example 9

Example 6 (20 mg) was dissolved in methanol (3 mL) and NH$_4$Cl (10 mg) in water (0.2 mL) was added followed by NaBH$_4$ (10 mg). After 10 mins the reaction was evaporated to dryness in-vacuo and the residue dissolved in water (3 mL) and washed with DCM. The aqueous extract was then purified by preparative HPLC to afford the product as an oil (4.23 mg).
MS m/z ([M+H]$^+$) 326.0. 1H $^1$H NMR (CD$_3$OD) δ 7.26 (d, 1H), 6.10 (d, 1H), 5.84 (s, 1H), 4.60 (d, 1H), 3.98 (d, 1H), 3.92-3.68 (m, 4H), 3.50 (s, 3H), 1.22 (s, 3H).

Similarly for Example 10.

Example 10

Example 7 (20 mg) yielded Example 10 (7.0 mg).
MS m/z ([M+H]$^+$) 402.0. 1H $^1$H NMR (CD$_3$OD) δ 7.28-7.18 (m, 6H), 6.08 (d, 1H), 5.75 (s, 1H), 5.45 (d, 1H), 5.38 (d, 1H), 4.62 (d, 1H), 4.01 (d, 1H), 3.93-3.89 (m, 1H), 3.80-3.68 (m, 3H), 1.19 (s, 3H).

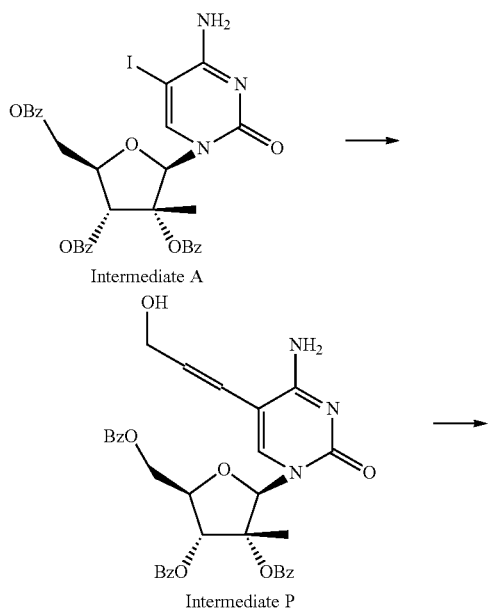

Scheme 7

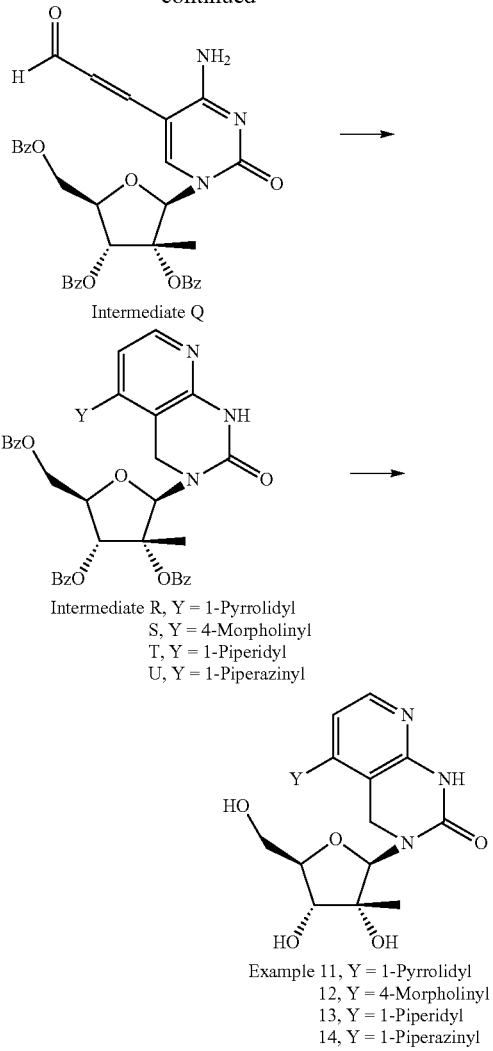

Intermediate R, Y = 1-Pyrrolidyl
S, Y = 4-Morpholinyl
T, Y = 1-Piperidyl
U, Y = 1-Piperazinyl Example 11, Y = 1-Pyrrolidyl
12, Y = 4-Morpholinyl
13, Y = 1-Piperidyl
14, Y = 1-Piperazinyl

Intermediate P

A degassed solution of intermediate A (695 mg) and propargyl alcohol (175 µl) was stirred in dry DMF (7 mL) under argon. CuI (38 mg) and PdCl$_2$(PPh$_3$)$_2$ (70 mg) were added followed by TEA (278 µl) and the mixture stirred at ambient temperature for 18 hrs. The solvent was evaporated in-vacuo and the residue partitioned between EtOAc and water. The organic layer was washed with water, dried (MgSO$_4$) and evaporated in-vacuo. The crude product was purified by radial chromatography on silica eluting with DCM then 5-10% MeOH/DCM to provide a gum (257 mg). MS m/z ([M+H]$^+$) 624.0, ([2M+H]$^+$) 1247.1.

Intermediate Q

Intermediate P (248 mg) was suspended in DCM (10 mL) and treated with Dess-Martin periodinane (338 mg) at ambient temperature. The reaction was diluted with DCM after 2 hrs and washed with saturated aqueous NaHCO$_3$. The organic phase was evaporated in-vacuo and the residue purified by radial chromatography on silica eluting with 5-10% MeOH/DCM to provide the product as a gum (263 mg). MS m/z ([M+H]$^+$) 621.8, ([2M+H]$^+$) 1242.9.

Intermediate R

Intermediate Q (30 mg) and pyrrolidine (14 mg) in acetonitrile (0.5 mL) were heated in a microwave reactor at 70° C. for 10 mins (initial power 200 W). The solvent was evaporated in-vacuo and the residue dissolved in EtOAc, washed with water then 1M HCl. The organic layer was washed with water, dried (MgSO$_4$) and evaporated in-vacuo to yield crude cyclised product (28 mg) used in the next step without further purification. The material was dissolved in MeOH (2 mL) and NaBH$_3$CN (13 mg) was added. After 1 hr the solvent was evaporated in-vacuo and the residue dissolved in EtOAc. The organic layer was washed successively with saturated aqueous NaHCO$_3$ and water, dried (MgSO4) and evaporated in-vacuo. The residue was purified by radial chromatography on silica eluting with 5% MeOH/DCM to yield the product as a gum (17 mg). MS m/z ([M+H]$^+$) 677.2.

Intermediates S, T and U were prepared by the general method described for Intermediate R using the appropriate amine and substituting NaBH$_4$ for NaBH$_3$CN.

Intermediate S

Intermediate Q (40 mg) yielded Intermediate S (21 mg). MS m/z ([M+H]$^+$) 693.1.

Intermediate T

Intermediate Q (62 mg) yielded Intermediate T (42 mg).
MS m/z ([M+H]$^+$) 691.2, ([2M+H]$^+$) 1381.0
Intermediate U
Intermediate Q (62 mg) yielded Intermediate U (28 mg). MS m/z ([M+H]$^+$) 692.1.

Example 11

Intermediate R (10 mg) was stirred with 7M NH$_3$ in MeOH (1 mL) at ambient temperature for 18 hrs. The reaction was evaporated to dryness in-vacuo and the residue dissolved in water and washed with DCM. The aqueous layer was then subjected directly to preparative HPLC. This process afforded the target compound as an oil (1.3 mg).

MS m/z ([M+H]$^+$) 365.1, ([2M+H]$^+$) 728.8.

1H $^1$H NMR (CD$_3$OD) δ 7.69 (d, 1H), 6.34 (d, 1H), 5.92 (s, 1H), 5.20 (d, 1H), 4.31 (d, 1H), 3.98-3.90 (m, 1H), 3.80-3.65 (m, 3H), 3.50-3.35 (m, 4H), 1.98-1.90 (m, 4H), 1.20 (s, 3H).

The general method for Example 11 was applied to the preparation of Examples 12-14.

Example 12

Intermediate S (20 mg) yielded compound 12 (2.4 mg) after purification by preparative HPLC.
MS m/z ([M+H]$^+$) 381.1, ([2M+Na]$^+$) 782.8.
1H $^1$H NMR (CD$_3$OD) δ 7.97 (d, 1H), 6.68 (d, 1H), 5.96 (s, 1H), 4.48 (d, 1H), 4.12 (d, 1H), 3.96-3.71 (m, 8H), 3.27-2.87 (m, 4H), 1.12 (s, 3H).

Example 13

Intermediate T (42 mg) yielded 4.27 mg compound 13 (4.3 mg) after purification by preparative HPLC.
MS m/z ([M+H]$^+$) 379.2, ([2M+H]$^+$) 756.9.
1H $^1$HNMR (CD$_3$OD) δ 7.93 (d, 1H), 6.65 (d, 1H), 5.97 (s, 1H), 4.42 (d, 1H), 4.07 (d, 1H), 3.93 (d, 1H), 3.82-3.71 (m, 3H), 3.04-2.87 (m, 4H), 1.86-1.60 (m, 6H), 1.13 (s, 3H).

Example 14

Intermediate U (27 mg) yielded compound 14 (2.1 mg) after purification by preparative HPLC.
MS m/z ([M+H]$^+$) 380.1, ([2M+Na]$^+$) 780.8.
1H $^1$H NMR (CD$_3$OD) δ 8.08 (d, 1H), 6.69 (d, 1H), 5.96, (s, 1H), 4.51 (d, 1H), 4.10 (d, 1H), 3.94-3.51 (m, 6H), 3.27-2.87 (m, 6H), 1.14 (s, 3H).

Example 15

Example 1 (31 mg) was dried overnight under high vacuum over P$_2$O$_5$ and then stirred with trimethyl phosphate (1.7 mL) at ambient temperature with oven-dried molecular sieves (4 Å) for 16 hrs. under argon. The reaction was cooled to 0° C., POCl$_3$ (31 µl) added and stirring continued for 2 hours before addition of Bu$_3$N (72 µl) followed by acetonitrile (0.5 mL) and tributylammonium pyrophosphate (190 mg). After a further 2 hrs. at 0° C. the reaction was quenched by pouring into ice-cold 1M triethylammonium bicarbonate buffer (10 mL, pH 8.5) and the aqueous layer washed with Et$_2$O (3×10 mL). The aqueous material was then lyophilized to give a white solid which was purified by preparative HPLC to afford the product (1.67 mg).

MS m/z ([M–H]$^-$) 547.6, ([M+3TEA+H]$^+$) 852.5.
$^{31}$P NMR (D$_2$O) δ –8.14 (m, 1P), –10.69 (m, 1P), –21.65 (m, 1P).
Biological Data In Vitro Anti-HCV Dose-response and Cytotoxicity HCV Replicon Assay The antiviral activity of test compounds were assayed in the stable HCV RNA-replicating cell line, AVA5, derived by transfection of the human hepatoblastoma cell line, Huh7 (Blight, et al., 2000, Sci. 290:1972). Concentrations of compounds were added to dividing cultures once daily for three days and intracellular HCV RNA levels and cytotoxicity assessed 24 hours after the last dose of the compound.

Intracellular HCV RNA levels were measured using standard blot hybridization techniques using triplicate cultures and levels of β-actin RNA were used to normalize HCV RNA levels in each sample. Cytotoxicity was measured using an established neutral red dye uptake assay (*B. E. Korba and J L. Gerin.* 1992. *Antivir. Res.* 19, 55-70) and the 50% effective antiviral concentrations (EC$_{50}$) and cytotoxic concentrations (CC$_{50}$) were calculated using a computer program for curve fitting.

Examples such as 1-14 were typically active in the replicon assay in the range 1 to >1000 µM and cytotoxic in the range 30 to >100 µM.

HCV Polymerase Inhibition Assay

HCV 3'UTR RNA template was synthesized, gel purified and quantified by spectrophotometry. The kinetic constant, K$_m$, was determined for the RNA template and for each GTP, CTP, ATP and UTP using a non-linear least square fit of initial rates as a function of substrate concentration assuming Michaelis-Menten kinetics.

Standard RdRp assays consisted of 30 nM RNA template and 25 nM HCV NS5bΔ21 (genotype 1b (Replizyme Ltd) in a 50 µl reaction mixture containing 20 mM Tris-HCl, 5 mM MgCl$_2$, 3 mM DTT, 0.05% BSA, 22 nM GTP, 600 nM ATP, 15 nM CTP, 30 nM UTP and 3 nM [α-$^{33}$P]GTP. Elongation reactions were initiated by the addition of NTPs and proceeded for 30 mins at 25° C. Reactions were quenched by the addition of 0.2 M EDTA and product formation was collected by filtration through Multiscreen plates (Millipore). Quantification of product formation was performed using TopCount (Perkin Elmer).

The inhibitor concentration at which the enzyme catalyzed rate is reduced by half ($IC_{50}$) was determined using a computer program for curve fitting Examples such as 15 were typically inhibitory of NS5b in the range 100 to >1000 μM.

The reference to any prior art in this specification is not, and should not be taken as, an acknowledgment or any form of suggestion that that prior art forms part of the common general knowledge.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention claimed is:
1. A compound of the formula (I) which may be a D-or L-nucleoside or nucleotide, or a salt thereof;

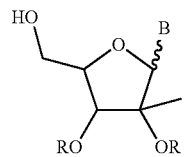

wherein:
each R is independently selected from the group consisting of H, $CF_3$, optionally substituted alkyl, optionally substituted alkenyl, optionally substituted alkynyl, optionally substituted aryl, optionally substituted acyl, optionally substituted cycloalkyl, optionally substituted cycloalkenyl, optionally substituted heteroaryl, optionally substituted heterocyclyl, and optionally substituted arylalkyl;
or C-5 monophosphate, diphosphate and triphosphate derivatives thereof, or C-5 mono, di or triphosphate mimics;
B is a group of formula (II)

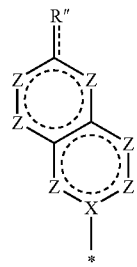
(II)

wherein, if Z is a participant in a π bond (double bond), Z is independently selected from N or C-G; or, if Z is not a participant in a π bond (double bond), Z is independently selected from O, S, Se, NR, NOR, $NNR_2$, CO, CS, CNR, SO, $S(O)_2$, SeO, $Se(O)_2$ or $C(G)_2$, wherein each G is independently selected from the group consisting of H, halogen, OR, SR, $NR_2$, NROR, $N_3$, COOR, CN, $CONR_2$, $C(S)NR_2$, C(=NR)$NR_2$, and R; and where any two adjacent Z are not both selected from O, S, and Se, or not both selected from CO, CS, CNR, SO, $S(O)_2$, SeO, and $Se(O)_2$;

wherein, if X is a participant in a π bond (double bond), X is C; or if X is not a participant in a π bond (double bond), X is CR or N;

wherein, if R" is a participant in a π bond (double bond), R" is O, S, Se, NR, NOR, and $NNR_2$; or if R" is not a participant in a π bond (double bond), R" is OR, SR, F, Cl, R, or SeR; and dashed lines (- - -) indicate a possible π or double bond.

2. A compound according to claim 1, or a salt thereof, wherein the base structure B is selected from the following formulae (XI) to (XXI)

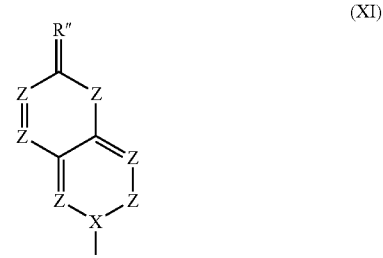
(XI)

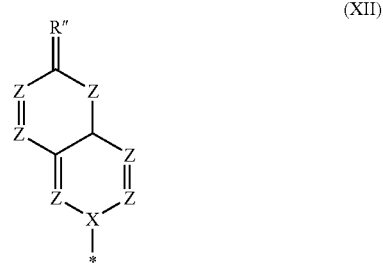
(XII)

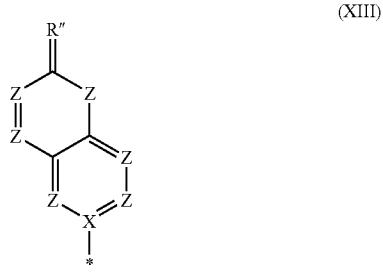
(XIII)

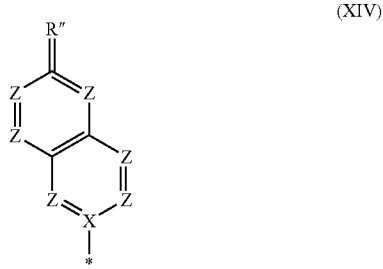
(XIV)

(XV) 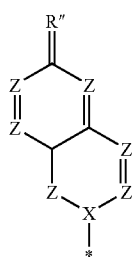
(XVI) 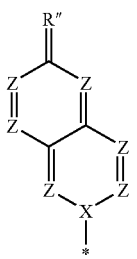
(XVII) 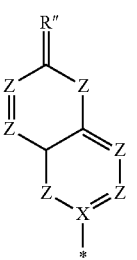
(XVIII) 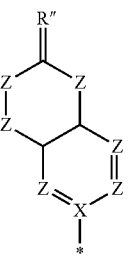
(XIX) 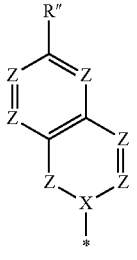
(XX) 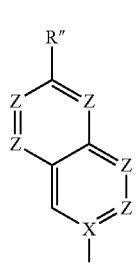
(XXI) 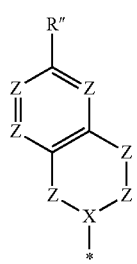
wherein Z, X and R" are as defined in claim 1.
3. A compound according to claim 1, or a salt thereof, wherein X is N.
4. A compound according to claim 1, or a salt thereof, wherein the base structure B is selected from the following:
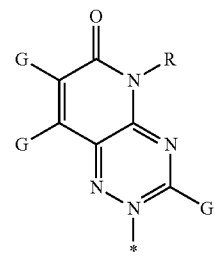
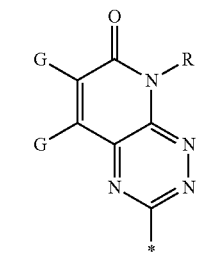
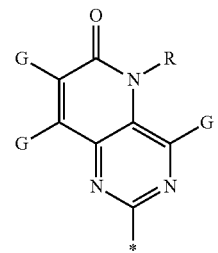
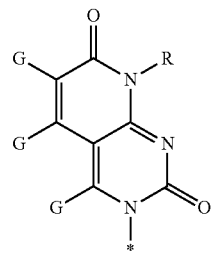
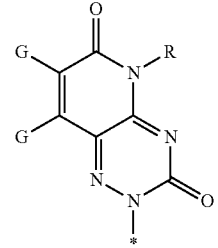
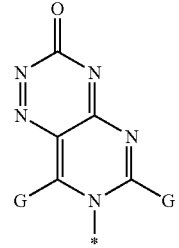

-continued

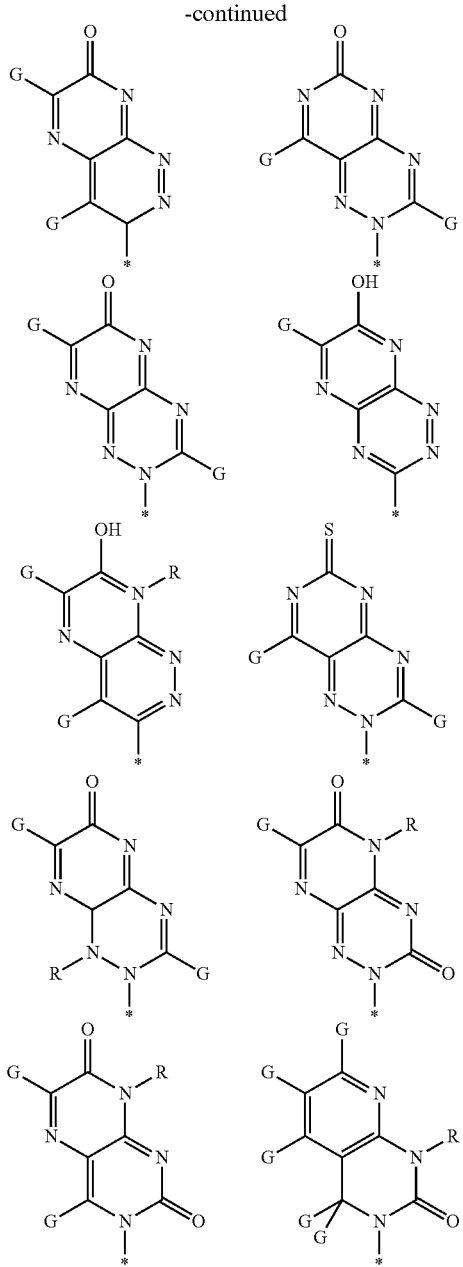

wherein G and R are as defined in claim 1.

5. A compound according to claim 1, or a salt thereof, wherein the base structure B is represented by formula IIa:

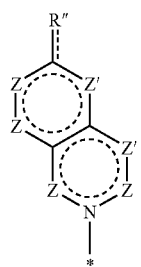

(IIa)

wherein each Z' is independently N (if a participant in a π bond) or NR (if not a participant in a π bond), and R", R and Z are as defined in claim 1.

6. A compound according to claim 1, or a salt thereof, wherein the base structure B is represented by the formula IIb:

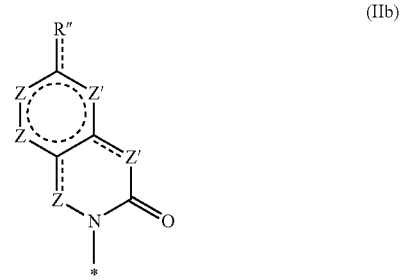

(IIb)

wherein each Z' is independently N (if a participant in a π bond) or NR (if not a participant in a π bond), and each Z is independently CG (if a participant in a π bond) or >C(G)$_2$ (if not a participant in a π bond), and wherein R" and G is as defined in claim 1.

7. A compound according to claim 1, or a salt thereof, wherein the base structure B is represented by formula IIc:

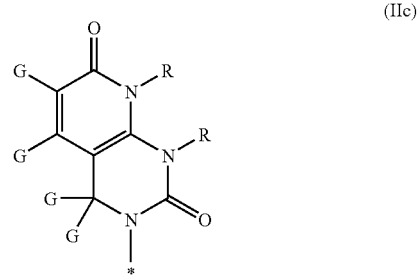

(IIc)

wherein R and G are as defined in claim 1.

8. A compound according to claim 1, or a salt thereof, wherein the base structure B is represented by the formula IId:

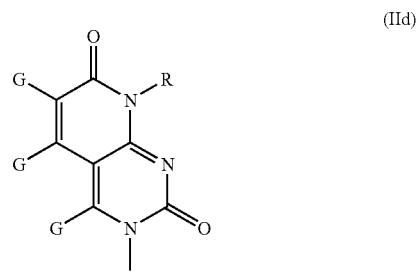

(IId)

wherein R and G are as defined in claim 1.

9. A compound according to claim 1, or a salt thereof, wherein the base structure B is represented by the formula IIe:

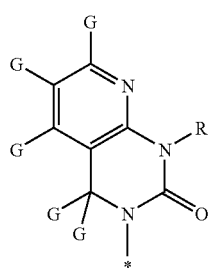
(IIe)

wherein R and G are as defined in claim 1.

10. A compound of formula (I) selected from the following formulae, or a salt thereof:

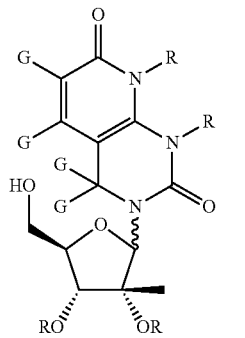 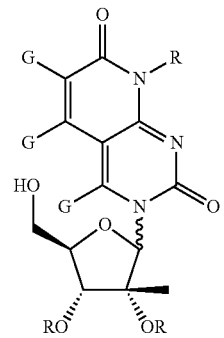

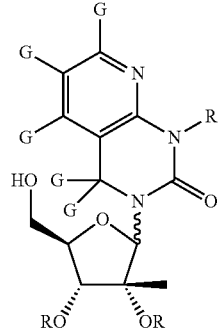

wherein:
- each R on the sugar moiety is independently selected from H, optionally substituted alkyl, optionally substituted alkenyl, optionally substituted alkynyl, optionally substituted aryl, optionally substituted acyl and optionally substituted arylalkyl;
- each R on the base moiety is independently selected from H, optionally substituted alkyl, optionally substituted aryl, optionally substituted heteroaryl, optionally substituted heterocyclyl, and optionally substituted arylalkyl;
- each G is independently selected from H, halogen, CF$_3$, optionally substituted alkyl, optionally substituted aryl, optionally substituted heteroaryl, optionally substituted heterocyclyl, and optionally substituted arylalkyl; and
- C-5 monophosphate, diphosphate and triphosphate derivatives thereof, or C-5 mono, di or triphosphate mimics.

11. A compound according to claim 1, or a salt thereof, wherein the sugar moiety is represented by the formula:

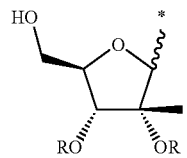

or C-5 monophosphate, diphosphate and triphosphate derivatives thereof, or C-5 mono, di or triphosphate mimics, wherein R is as defined in claim 1.

12. A compound according to claim 1, or a salt thereof, wherein the sugar moiety is represented by the formula:

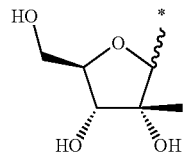

or C-5 monophosphate, diphosphate and triphosphate derivatives thereof, or C-5 mono, di or triphosphate mimics.

13. A compound according to claim 1, or a salt thereof, which is a β anomer.

14. A compound according to claim 1, or a salt thereof, selected from

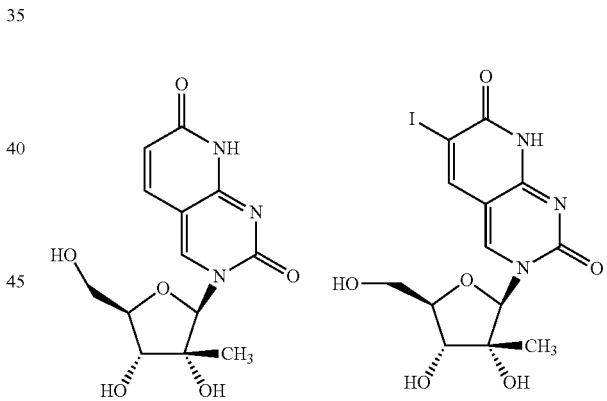

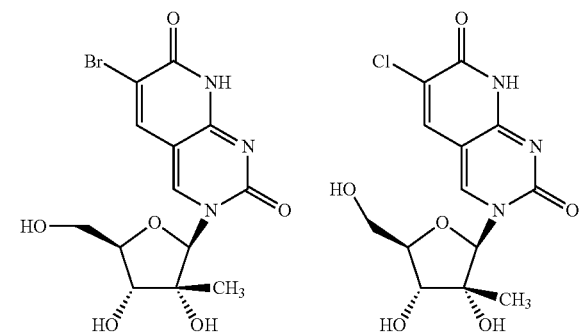

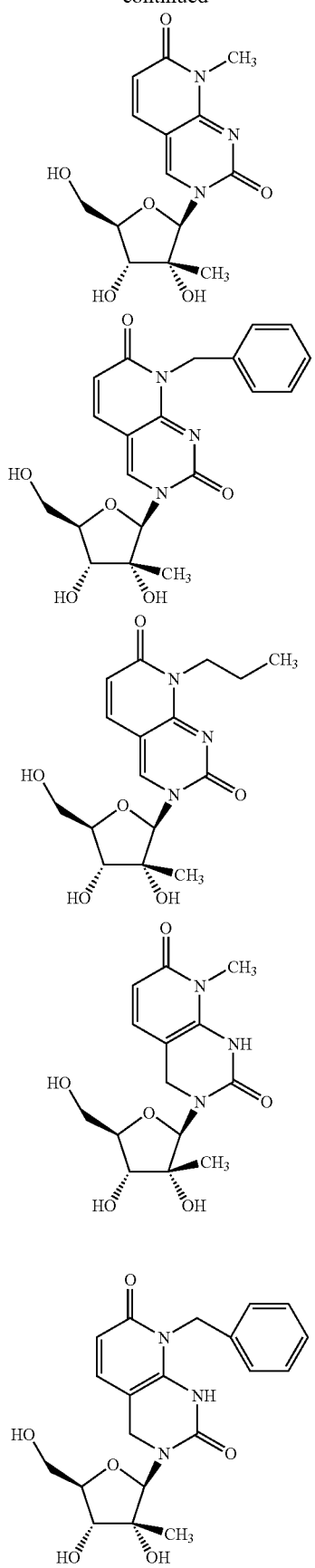
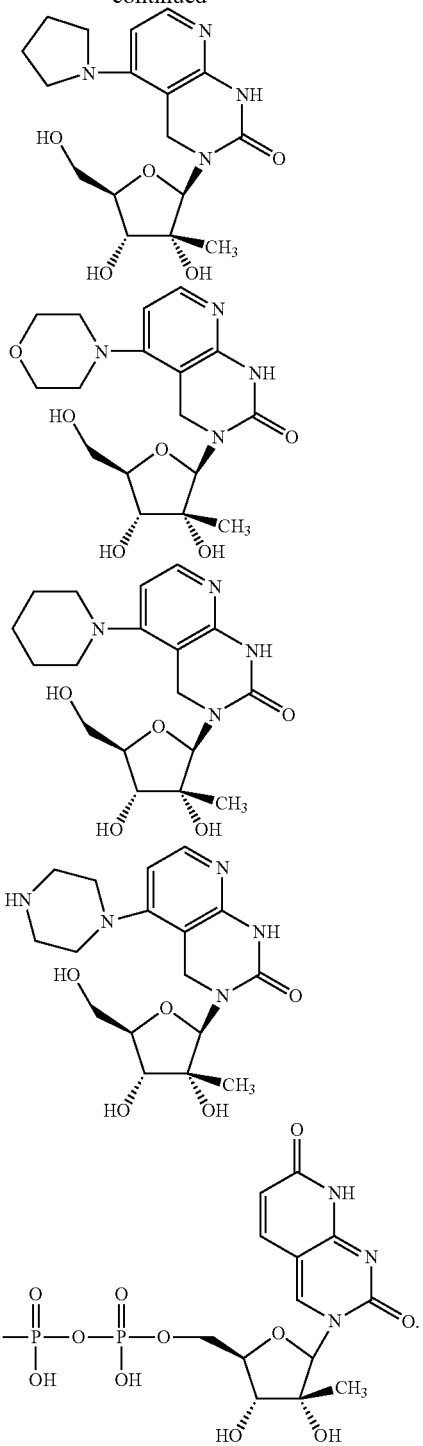

15. A pharmaceutical composition comprising a compound according to claim 1 or a salt thereof, and at least one pharmaceutically acceptable carrier or diluent.

16. A pharmaceutical composition according to claim 15 for use in the treatment of a viral infection.

17. A pharmaceutical composition according to claim 16, wherein the virus is the hepatitis C virus.

18. A pharmaceutical composition according to claim 15 further comprising one or more antiviral or antibacterial agents.

19. A pharmaceutical composition according to claim 18, wherein the antiviral agents are selected from the group selected from interferon and interferon derivatives, IMPDH inhibitors, antiviral nucleosides, polymerase inhibitors and protease inhibitors.

20. A pharmaceutical composition according to claim 19, wherein the composition comprises interferon or ribavirin.

* * * * *